(12) United States Patent
DeAscanis et al.

(10) Patent No.: US 9,709,463 B2
(45) Date of Patent: Jul. 18, 2017

(54) METHOD AND SYSTEM FOR SURFACE PROFILE INSPECTION OF OFF-LINE INDUSTRIAL GAS TURBINES AND OTHER POWER GENERATION MACHINERY

(71) Applicant: Siemens Energy, Inc., Orlando, FL (US)

(72) Inventors: Joshua DeAscanis, Oviedo, FL (US); Clifford Hatcher, Jr., Orlando, FL (US); David Letter, Deland, FL (US)

(73) Assignee: Siemens Energy, Inc., Orlando, FL (US)

( * ) Notice: Subject to any disclaimer, the term of this patent is extended or adjusted under 35 U.S.C. 154(b) by 248 days.

(21) Appl. No.: 14/732,982

(22) Filed: Jun. 8, 2015

(65) Prior Publication Data
US 2015/0300920 A1 Oct. 22, 2015

Related U.S. Application Data

(63) Continuation-in-part of application No. 13/972,000, filed on Aug. 21, 2013, now Pat. No. 9,116,071,
(Continued)

(51) Int. Cl.
*G01M 15/14* (2006.01)
*G01N 21/954* (2006.01)
(Continued)

(52) U.S. Cl.
CPC .......... *G01M 15/14* (2013.01); *F01D 21/003* (2013.01); *G01N 21/954* (2013.01);
(Continued)

(58) Field of Classification Search
USPC ....................................... 73/112.01
See application file for complete search history.

(56) References Cited

U.S. PATENT DOCUMENTS 5,102,221 A 4/1992 Desgranges et al.
5,164,826 A 11/1992 Dailey
(Continued)

FOREIGN PATENT DOCUMENTS

EP 0907077 4/1999

OTHER PUBLICATIONS

Co-pending U.S. Appl. No. 13/971,938, filed Aug. 21, 2013.
(Continued)

*Primary Examiner* — Eric S McCall

(57) ABSTRACT

Internal components of power generation machines, such as gas or steam turbines, are inspected with a laser profilometer inspection system that is inserted and positioned within the turbine, for example through an inspection port that is in communication with an open inter-row spacing volume between an opposing turbine vane and turbine blade row. Component surface profile scans are performed to determine relative profile heights along a two-dimensional scan line generated by the profilometer. Three-dimensional profile information is obtained by translating the scan line across the surface. Real time profile information is gathered without physical contact, which is helpful for extracting off-line engineering information about component surface conditions, including surface spallation, perforation, and gaps between components. The system is capable of determining blade tip gap between a turbine blade tip and its opposing abradable surface in the turbine casing.

20 Claims, 28 Drawing Sheets

Related U.S. Application Data which is a continuation-in-part of application No. 13/362,352, filed on Jan. 31, 2012, now Pat. No. 8,713,999.

(60) Provisional application No. 61/692,409, filed on Aug. 23, 2012.

(51) Int. Cl.
*F01D 21/00* (2006.01)
*G02B 23/24* (2006.01)
*G01M 15/02* (2006.01)

(52) U.S. Cl.
CPC ..... *G02B 23/2484* (2013.01); *G02B 23/2492* (2013.01); *G01M 15/02* (2013.01)

(56) References Cited

U.S. PATENT DOCUMENTS

| | | |
|---|---|---|
| 5,349,850 A | 9/1994 | Young |
| 6,317,387 B1 | 11/2001 | D'Amaddio |
| 6,992,315 B2 | 1/2006 | Twerdochlib |
| 7,068,029 B2 | 6/2006 | Hatcher |
| 7,271,894 B2 | 9/2007 | Devitt et al. |
| 7,489,811 B2 | 2/2009 | Brummel |
| 7,956,326 B1 | 6/2011 | Kychakoff et al. |
| 8,151,647 B2 * | 4/2012 | Twerdochlib .......... G01H 1/006 702/56 |
| 8,184,151 B2 | 5/2012 | Zombo |
| 8,299,785 B2 | 10/2012 | Bousquet et al. |
| 8,713,999 B2 | 5/2014 | Hatcher |
| 8,922,640 B2 | 12/2014 | Hatcher et al. |
| 2004/0051525 A1 | 3/2004 | Hatcher et al. |
| 2004/0193016 A1 | 9/2004 | Root |
| 2005/0199832 A1 | 9/2005 | Twerdochlib |
| 2005/0200355 A1 | 9/2005 | Hatcher |
| 2006/0088793 A1 | 4/2006 | Brummel et al. |
| 2007/0129604 A1 | 6/2007 | Hatcher |
| 2007/0157733 A1 | 7/2007 | Litzenberg |
| 2007/0296964 A1 | 12/2007 | Nishimura et al. |
| 2009/0078053 A1 * | 3/2009 | Twerdochlib .......... G01H 1/006 73/661 |
| 2011/0018530 A1 | 1/2011 | Bousquet et al. |
| 2011/0267428 A1 | 11/2011 | George et al. |
| 2012/0154594 A1 | 6/2012 | Xie et al. |
| 2012/0281084 A1 | 11/2012 | Hatcher |
| 2013/0194412 A1 | 8/2013 | Hatcher |
| 2013/0194413 A1 | 8/2013 | Hatcher |
| 2014/0064924 A1 * | 3/2014 | Warren .................. G01B 7/14 415/118 |
| 2014/0168420 A1 | 6/2014 | Naderhirn |
| 2015/0054939 A1 * | 2/2015 | DeAscanis ........... G01M 15/14 348/82 |
| 2015/0199805 A1 * | 7/2015 | Hatcher, Jr. ............. G06T 7/004 348/135 |
| 2016/0177771 A1 * | 6/2016 | Hatcher, Jr. ............. F01D 17/02 415/118 |

OTHER PUBLICATIONS

Co-pending U.S. Appl. No. 13/362,417, filed Jan. 31, 2012.
Co-pending U.S. Appl. No. 13/362,352, filed Jan. 31, 2012, now U.S. Pat. No. 8,713,999 issued on May 6, 2014.
Co-pending U.S. Appl. No. 13/362,387, filed Jan. 31, 2012, now U.S. Pat. No. 8,922,640 issued on Dec. 30, 2014.
Co-pending U.S. Appl. No. 13/972,000, filed Aug. 21, 2013.
Micro-Epsilon USA, Raleigh, NC USA "scanCONTROL// 2D/3D laser scanner (laser profile sensors)" product description (publication date unknown).

* cited by examiner

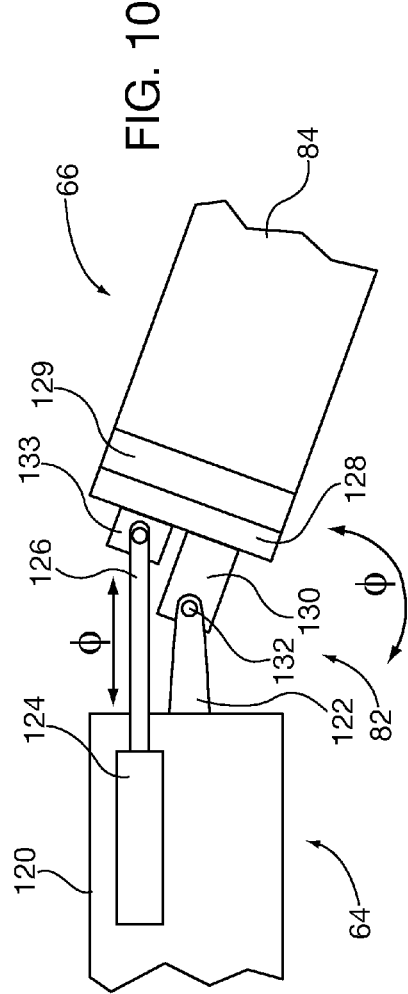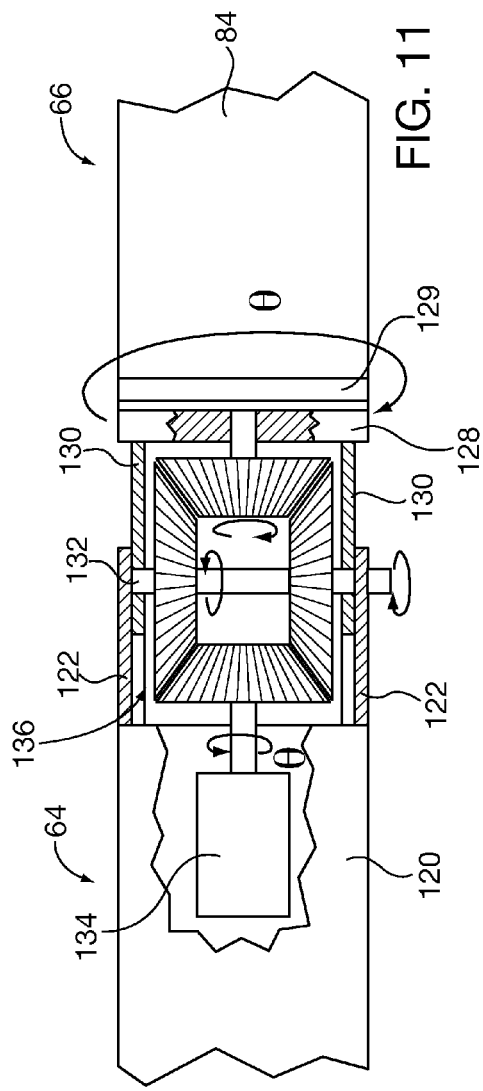

METHOD AND SYSTEM FOR SURFACE PROFILE INSPECTION OF OFF-LINE INDUSTRIAL GAS TURBINES AND OTHER POWER GENERATION MACHINERY

PRIORITY CLAIM AND REFERENCE TO CO-PENDING APPLICATIONS

This application is a continuation-in-part of United States utility patent application entitled "System And Method For Visual Inspection And 3D White Light Scanning Of Off-Line Industrial Gas Turbines And Other Power Generation Machinery", filed, Aug. 21, 2013 and assigned Ser. No. 13/972000; which in turn claims the benefit of U.S. provisional patent application entitled "Vision Scope—3D Scanner Tip for Visual Inspection and Measurement" filed Aug. 23, 2012 and assigned Ser. No. 61/692,409; and which is also a continuation-in-part of United States utility patent application entitled "System And Method For Automated Optical Inspection Of Industrial Gas Turbines And Other Power Generation Machinery With Multi-Axis Inspection Scope", filed Jan. 31, 2012 and assigned Ser. No. 13/362,352, now U.S. Pat. No. 8,713,999 ; the entire contents of each of these claimed priority applications is incorporated by reference herein.

This application also incorporates by reference herein co-pending co-pending United States utility patent application entitled "System And Method For Optical Inspection Of Off-Line Industrial Gas Turbines And Other Power Generation Machinery While In Turning Gear Mode", filed Aug. 21, 2013, Ser. No. 13/971,938, that in turn claims the benefit of U.S. provisional patent application entitled "Hybrid Scope—Turbine Combustor Hardware Visual Inspection Tooling That Can Also Be Used To Inspect The Row 1 Turbine Blades While They Are On Turning Gear (1-1000 rpm)" filed Aug. 23, 2012 and assigned Ser. No. 61/692,393. This application also incorporates by reference herein United States utility patent application entitled "System And Method For Automated Optical Inspection Of Industrial Gas Turbines And Other Power Generation Machinery", filed Jan. 31, 2012 and assigned Ser. No. 13/362,417; and United States utility patent application entitled "System And Method For Automated Optical Inspection Of Industrial Gas Turbines And Other Power Generation Machinery With Multi-Axis Inspection Scope", filed Jan. 31, 2012 and assigned Ser. No. 13/362,387, now U.S. Pat. No. 8,992,640.

TECHNICAL FIELD

The invention relates to optical camera systems for non-destructive internal inspection and real time component surface relative dimensional measurement of industrial turbines and other power generation machinery, including by way of non-limiting example gas turbines and steam turbines and generators. More particularly, those internal components are inspected with a laser profilometer inspection system that is inserted and positioned within the power generation machine, for example through an inspection port that is in communication with inter-row spacing volume between an opposing turbine vane and turbine blade row within a gas turbine engine. Component surface profile scans are performed to determine relative profile heights along a two-dimensional scan line generated by the profilometer. Three-dimensional profile information is obtained by translating the scan line across the surface. Real time profile information is gathered without physical contact, which is helpful for extracting off-line engineering information about component surface conditions, including surface spallation, perforation, and gaps between components. In exemplary embodiments, the system is capable of determining blade tip gap between a turbine blade tip and its opposing abradable surface in the turbine casing. Automatic camera positioning and scan image capture can be initiated automatically or after receipt of operator permission.

BACKGROUND

Power generation machinery, such as steam or gas turbines, are often operated continuously with scheduled inspection and maintenance periods, at which time the turbine is taken off line and shut down. By way of example, a gas turbine engine often will be operated to generate power continuously for approximately 4000 hours, thereupon it is taken off line for routine maintenance, inspection, and repair of any components identified during inspection. Taking a gas turbine off line and eventually shutting it down completely for scheduled maintenance is a multi-day project. Some turbine components, such as the turbine rotor section, are operated at temperatures exceeding 1000° C. (1832° F.). The turbine requires 48-72 hours of cooling time to achieve ambient temperature before complete shutdown in order to reduce likelihood of component warping or other deformation. During the shutdown phase the turbine rotor rotational speed is spooled down from operating speed of approximately 3600 RPM to a speed of approximately 120 RPM or less in "turning gear mode" where the rotor is externally driven by an auxiliary drive motor, in order to reduce likelihood of rotor warping. Other turbine components, such as the turbine housing, are also cooled slowly to ambient temperature.

Once the turbine is cooled to ambient temperature over the course of up to approximately 72 hours internal components of the now static turbine can be inspected with optical camera inspection systems. Known optical camera inspection systems employ rigid or flexible optical bore scopes that are inserted into inspection ports located about the turbine periphery. The bore scope is manually positioned so that its field of view encompasses an area of interest within the turbine, such as one or more vanes or blades, combustor baskets, etc. A camera optically coupled to the bore scope captures images of objects of interest within the field of view for remote visualization and archiving (if desired) by an inspector.

If a series of different images of different areas of interest within a given turbine inspection port are desired, the operator must manually re-position the camera inspection system bore scope to achieve the desired relative alignment of internal area of interest and the field of view. Relative alignment can be achieved by physically moving the bore scope so that its viewing port is positioned proximal a static area of interest. Examples of such relative movement of bore scope and static turbine component are by inserting a bore scope in different orientations within a static combustor or radially in and out of space between a vane and blade row within the turbine section. Relative alignment can also be achieved by maintaining the bore scope viewing port in a static position and moving the turbine internal component of interest into the static viewing field. An example of relative movement of turbine internal component and static bore scope is inspection of different blades within a blade row by manually rotating the turbine rotor sequentially a few degrees and capturing the image of a blade. The rotor is rotated sequentially to align each desired individual blade in the row within the camera-viewing field.

Complete turbine inspection requires multiple manual relative repositioning sequences between the camera inspection system viewing port and areas of interest within the turbine by a human inspector. Inspection quality and productivity is subject to the inspection and manipulation skills of the inspector and inspection team. Inspection apparatus positioning is challenging due to the complex manipulation paths between components in a gas turbine. For example, insertion of a bore scope through a combustor inspection port in order to inspect the leading edge of first row vanes or related supports requires compound manipulations. Improper positioning of inspection apparatus within a turbine potentially can damage turbine internal components. Often an inspection team of multiple operators is needed to perform a manual inspection using known inspection methods and apparatus. In summary, known manual camera inspection procedures and inspection system manipulation are time consuming, repetitive in nature, and often require assistance of an inspection team of multiple personnel. The "human factor" required for known manual camera inspection procedures and inspection system manipulation introduces undesirable inspection process variances based on human skill level differences. Given human skill variances, some inspection teams are capable of completing inspections in less time, achieve better image quality, and have lower inspection damage risk than other teams. Ideally, skills of a high performing inspection team could be captured for use by all teams.

It is also desirable to obtain dimensional information about gas or steam turbines, including gas side internal structures within an industrial gas turbine inspection for extraction of structural information that is useful for off-line engineering studies. For example, it is desirable to obtain structural information about gas side combustor and transition components within the gas side of a gas turbine and generate CAD or other computer images when engineering data files are not available. Previously structural information was obtained by tearing down the turbine after completion of the cool down cycle and thereafter physically inspecting the components with measurement instruments, such as coordinate measurement systems. Physical measurement data were thereafter used to construct CAD or other data files long after engine cool down, thereby adding delay to the maintenance schedule.

It is preferable to gather such structural data prior to turbine tear down so that replacement components can be ordered or fabricated in parallel with the start of maintenance operations rather than wait for visual and/or physical inspection after engine tear down. If dimensional data, preferably with visual data, of turbine internal components can be obtained early and easily in the earliest possible stages of the cool down cycle—for example when the rotor is spinning in the long turning gear mode part of the cool down cycle—components needing repair can be prioritized for replacement, refurbishment and/or other repair days before the turbine rotor comes to a complete rest.

It is also desirable to obtain quantitative information about relative dimensional surface profile of components within power generation machines, such as turbine blade or vane thermal barrier coat (TBC) layer variations, perforations in such surfaces, blade tip gap between turbine blade tips and their opposed abradable surfaces of the turbine engine casing and seal gaps between stationary turbine vane central hubs and their opposing rotating rotor seals. It is preferable to gather such surface profile relative dimensional data prior to turbine tear down, for the previously stated reasons respecting structural data gathering. Surface profile data gathering can be performed separate and apart from other types of visual inspection data gathering.

In many field service applications it is also desirable to gather multiple types of visual inspection data, including dimensional and/or surface profile data and/or a general video record of power generation machine internal components during a single pre-teardown inspection cycle.

SUMMARY OF INVENTION

Internal components of power generation machines, such as gas or steam turbines, are inspected with a laser profilometer inspection system that is inserted and positioned within the turbine, for example through an inspection port that is in communication with an open inter-row spacing volume between an opposing turbine vane and turbine blade row. Component surface profile scans are performed to determine relative profile heights along a two-dimensional scan line generated by the profilometer. Three-dimensional profile information is obtained by translating the scan line across the surface. Real time profile information is gathered without physical contact, which is helpful for extracting off-line engineering information about component surface conditions, including surface spallation, perforation, and gaps between components. The system is capable of determining blade tip gap between a turbine blade tip and its opposing abradable surface in the turbine casing. In some embodiments, the inspection system enables real time surface profile relative dimensional measurement, which is helpful for extracting off-line engineering information about the scanned structures. In some embodiments, the system facilitates extraction of dimensional information while the turbine is in cool down mode prior to maintenance and facilitates gathering of other visual inspection information.

In embodiments of the invention the inspection scope has a base that is affixed to an off-line gas turbine combustion section, with the inspection scope being inserted through a combustor pilot nozzle port, through the transition, with the profilometer field of view and any other visual inspection cameras affixed to the scope camera head being oriented to capture surface profile dimensional images of gas side combustion section internal components, including the combustor and transition, as well as turbine section internal components, including by way of example stator vanes, turbine blades, turbine blade tip gap measurements or other gap measurements between internal components therein.

An embodiment of the invention is directed to a method for non-contact, internal inspection, including relative height sizing of component surface profiles, within an assembled power generation machine. An internal inspection system apparatus is provided; the system having a base along with an inspection scope having a proximal end that is coupled to the base. The inspection scope further has an extendable elongated body defining a central axis, extended and driven by a linear drive that is capable of remote actuation by a control system; and a distal end that is insertable into an inspection port of and maneuvering within an internal cavity of an assembled power generation machine to an internal area of interest. A laser profilometer head is coupled to the inspection scope distal end, which includes a laser profilometer having a two-dimensional height and width scanning field of view that is capable of remote scanning field image capture by, and image transmission to a control system. The system also includes a control system coupled to the linear drive and the laser profilometer, for maneuvering the laser profilometer scanning field of view to an area of interest within the assembled power generation machine by actuation of the linear drive, for capturing a scanning field of view image thereof, and for converting said image into relative two-dimensional height/width relative sizing data. The method is performed on an assembled power generation machine, such as a steam or combustion turbine having an inspection port that is in communication with an internal cavity and internal area of interest in the machine. The base is attached to the machine in a fixed position relative to the inspection port. The inspection scope distal end, including the laser profilometer head, is inserted into the inspection port and the inspection scope proximal end is coupled to the base. The laser profilometer scanning field of view is maneuvered within the internal cavity to an internal area of interest by actuating the linear drive with the control system. The profilometer scanning field of view image data of the area of interest is captured by actuating the laser profilometer with the control system; whereupon the captured image data is transferred to the control system. Captured image data is converted into two-dimensional height/width relative sizing data of the area of interest with the control system.

Another embodiment of the invention is directed to a method for measuring blade tip gap in an assembled turbine engine power generation machine, having an inspection port in communication with open inter-row spacing volume between an opposing turbine vane and turbine blade row, comprising. The method is practiced with an internal inspection system apparatus having a base and an inspection scope having a proximal end for coupling to the base. The inspection scope has an extendable elongated body defining a central axis, extended and driven by a linear drive that is capable of remote actuation by a control system; and a distal end that is insertable into an inspection port of, and maneuvering within an internal cavity of the assembled power generation machine to an internal area of interest. A laser profilometer head is coupled to the inspection scope distal end, and includes a laser profilometer having a two-dimensional height and width scanning field of view that is capable of remote scanning field image capture by, and image transmission to a control system. The control system is coupled to the linear drive and the laser profilometer, for maneuvering the laser profilometer scanning field of view to an area of interest within the assembled power generation machine by actuation of the linear drive, for capturing a scanning field of view image thereof, and for converting said image into two-dimensional height/width relative sizing data. The inspection scope is inserted and coupled to the engine in a fixed position relative to the inter-row communicating inspection port, such as a combustor nozzle pilot port. The laser profilometer scanning field of view is maneuvered within the inter-row spacing volume to scan turbine blade tip gap defined between a turbine blade tip surface and its corresponding opposed circumferential abradable surface of the turbine engine casing, by actuating the linear drive with the control system; and then capturing the tip gap scanning field of view image data by actuating the laser profilometer with the control system. The corresponding tip gap captured image data is transferred to the control system, which converts the captured image data into a two-dimensional height/width relative sizing data of the corresponding blade tip and abradable opposed surfaces defining the tip gap. The blade tip gap is determined with the relative sizing data.

Yet another embodiment of the invention features a system for non-contact, internal inspection, including relative height sizing of component surface profiles, within an assembled power generation machine. The system comprises a base for affixation to a power generation machine inspection port; and an inspection scope having a proximal end coupled to the base. The inspection scope has an extendable elongated body defining a central axis, extended and driven by a linear drive that is capable of remote actuation by a control system; and a distal end that is insertable into an inspection port of and maneuvering within an internal cavity of an assembled power generation machine to an internal area of interest. A laser profilometer head is coupled to the inspection scope distal end, and includes a laser profilometer having a two-dimensional height and width scanning field of view that is capable of remote scanning field image capture by, and image transmission to a control system. The control system is coupled to the linear drive and the laser profilometer, for maneuvering the laser profilometer scanning field of view to an area of interest within the assembled power generation machine by actuation of the linear drive, for capturing a scanning field of view image thereof, and for converting said image into two-dimensional height/width relative sizing data.

The respective features of the exemplary embodiments of the invention that are described herein may be applied jointly or severally in any combination or sub-combination.

BRIEF DESCRIPTION OF DRAWINGS

The exemplary embodiments of the invention are further described in the following detailed description in conjunction with the accompanying drawings, in which:

FIG. 10 is a schematic elevational view of a camera head articulation and rotation (pan) mechanism of the optical camera inspection system of FIG. 5, showing the $\Phi$ and $\theta$ degrees of motion;

FIG. 11 is a schematic plan view of a camera head articulation and rotation (pan) mechanism of FIG. 10;

To facilitate understanding, identical reference numerals have been used, where possible, to designate identical elements that are common to the figures.

DETAILED DESCRIPTION

Figure 1:
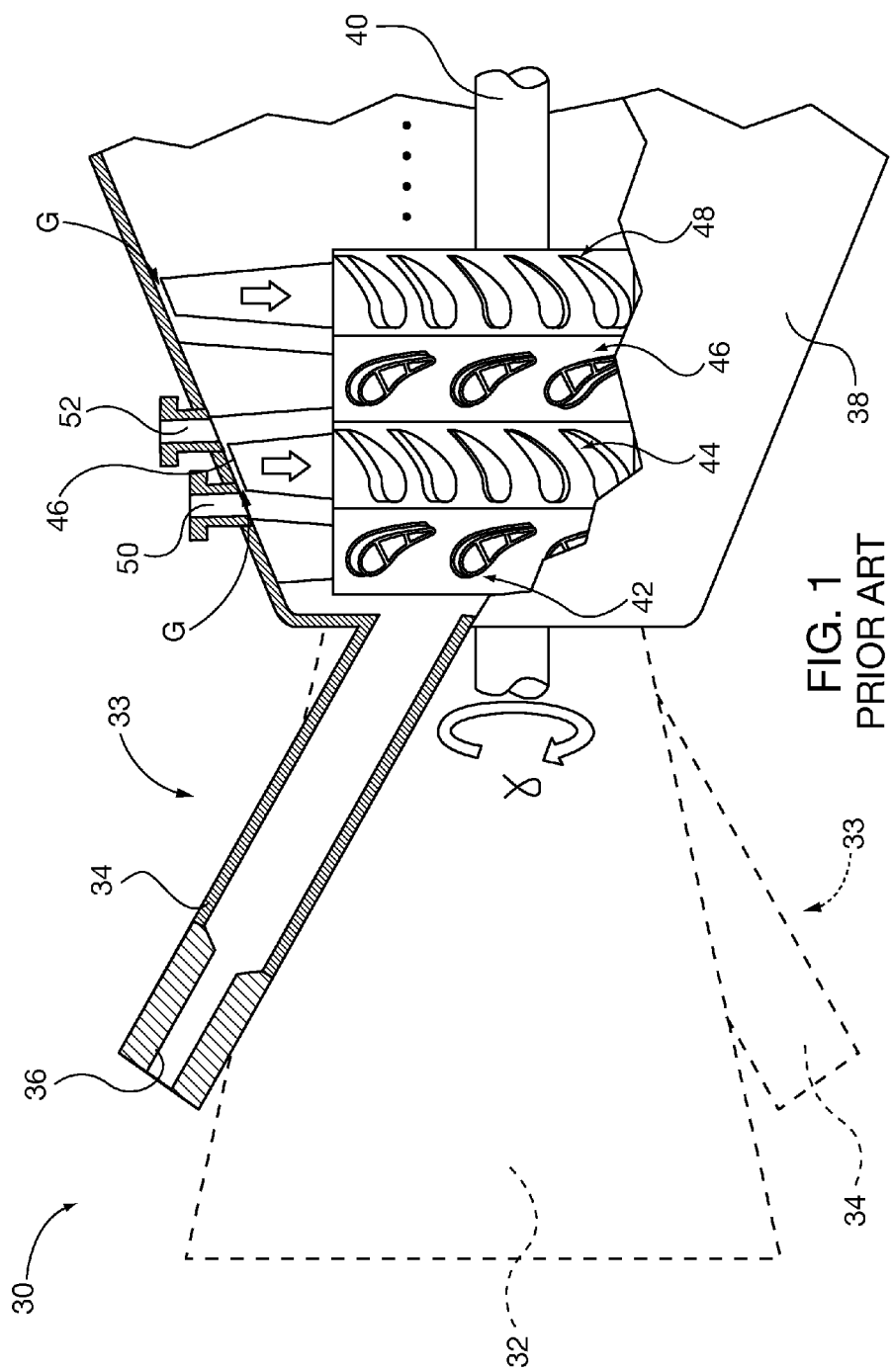
FIG. 1 is a partial cross sectional schematic view of a known gas turbine, including its combustion section.

Exemplary embodiments of the invention are used for inspection of internal component surfaces of power generation machines, such as gas or steam turbines. Those component surfaces are inspected with a laser profilometer inspection system that is inserted and positioned within the turbine, for example through a gas turbine combustor nozzle port or other type of inspection port that is in communication with an open inter-row spacing volume between an opposing turbine vane and turbine blade row. Component surface profile scans are performed to determine relative profile heights along a two-dimensional scan line generated by the profilometer. Three-dimensional profile information is obtained by translating the scan line across the surface. Real time profile information is gathered without physical contact, which is helpful for extracting off-line engineering information about component surface conditions, including surface spallation, perforation, and gaps between components. The system is capable of determining blade tip gap between a turbine blade tip and its opposing abradable surface in the turbine casing. In some embodiments, the inspection system enables real time surface profile relative dimensional measurement while the turbine engine is in cool down mode prior to maintenance and facilitates gathering of other visual inspection information.

In some embodiments, the optical camera inspection system is capable of automatically positioning the respective laser profilometer, 3D and optical cameras fields of view (FOV) to an area of interest within the machinery and capturing images without human intervention. Automatic camera positioning and image capture can be initiated automatically or after receipt of operator permission. Alternatively, the system may be human-operated in "manual" mode.

Inspection Scope System Overview

Referring generally to FIGS. 1, 4 and 27-37, embodiments of the present invention facilitate automated or manually controlled, off-line remote relative surface profile dimensional scanning and optional visual inspection of power generation machinery, such as gas turbine 30, internal component surfaces. Exemplary internal component surfaces include those in the turbine engine 30 compressor section 32; combustion section 33 combustors and transitions 34; and turbine section 38 turbine vanes 42 and blades 44. Blade tip gap G and other gaps between components within the engine 30 are obtained in embodiments described herein.

Embodiments of the inspection system described herein enable inspection of offline turbines by attaching a remote-actuated inspection scope 60, which include a selectively detachable laser profilometer head 466, or 3D scanner head 88', or a camera inspection head 88 to turbine inspection ports such as a combustor nozzle port 36 or circumferentially oriented inter-row ports 52, 54. Upon attachment to the engine 30, the inspection scope 60 is selectively positioned (manually by an operator or automatically without an operator) via internal motion control servo motors that are under command of a motion control system, such as the motion control system 400 that is coupled to the inspection scope 60 and attached laser profilometer head 466. Depending upon which data gathering head is coupled to the inspection scope 60 (e.g., the laser profilometer head 466) any one or more of surface profile relative dimensional data, three dimensional scan data or visual image data are acquired, captured, and if desired archived for further analysis.

Articulated Inspection Scope

Figure 2:
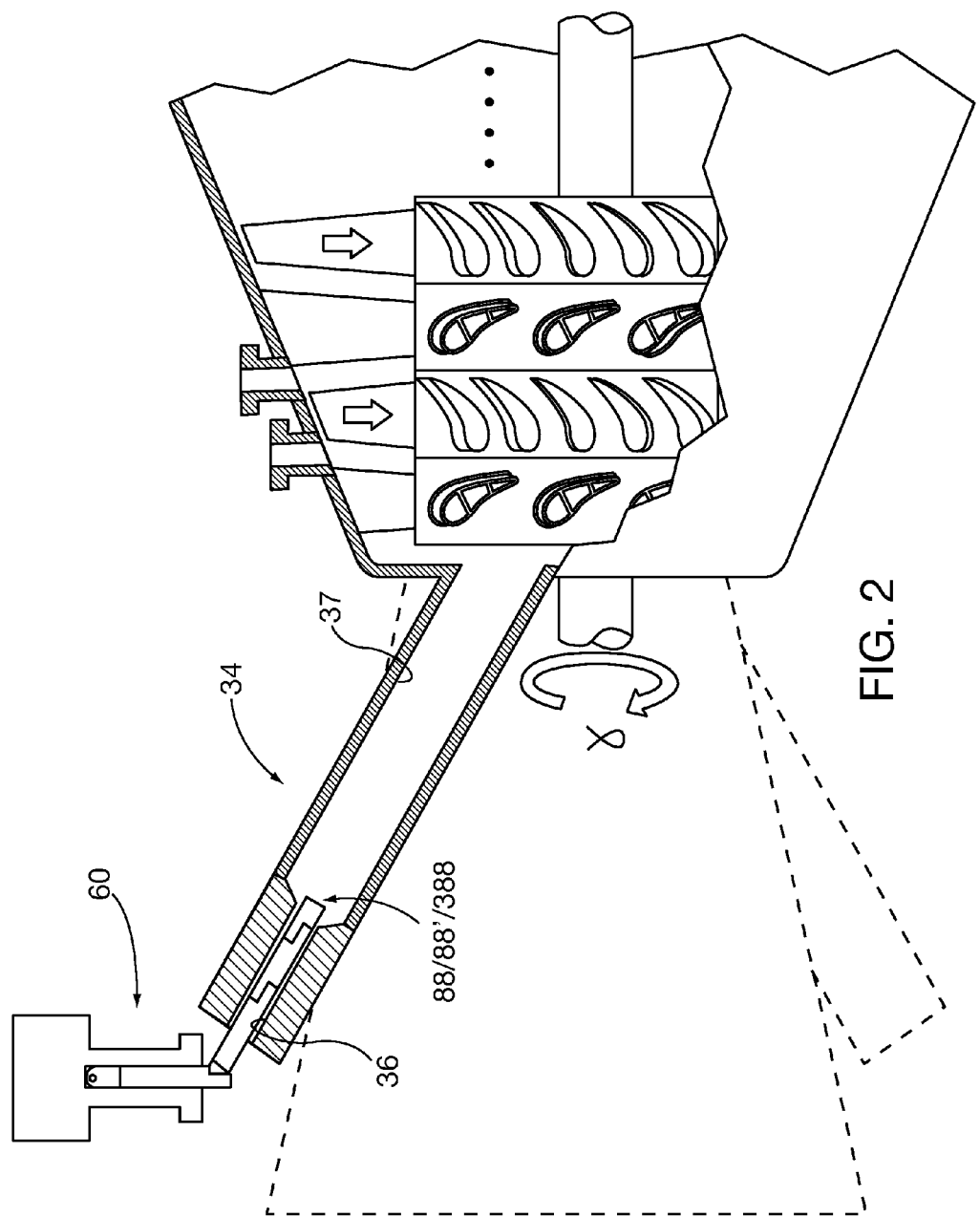
FIG. 2 is a partial cross sectional schematic view of a known gas turbine showing partial insertion of an optical camera inspection system described in the present application into a combustor nozzle port.
Figure 3:
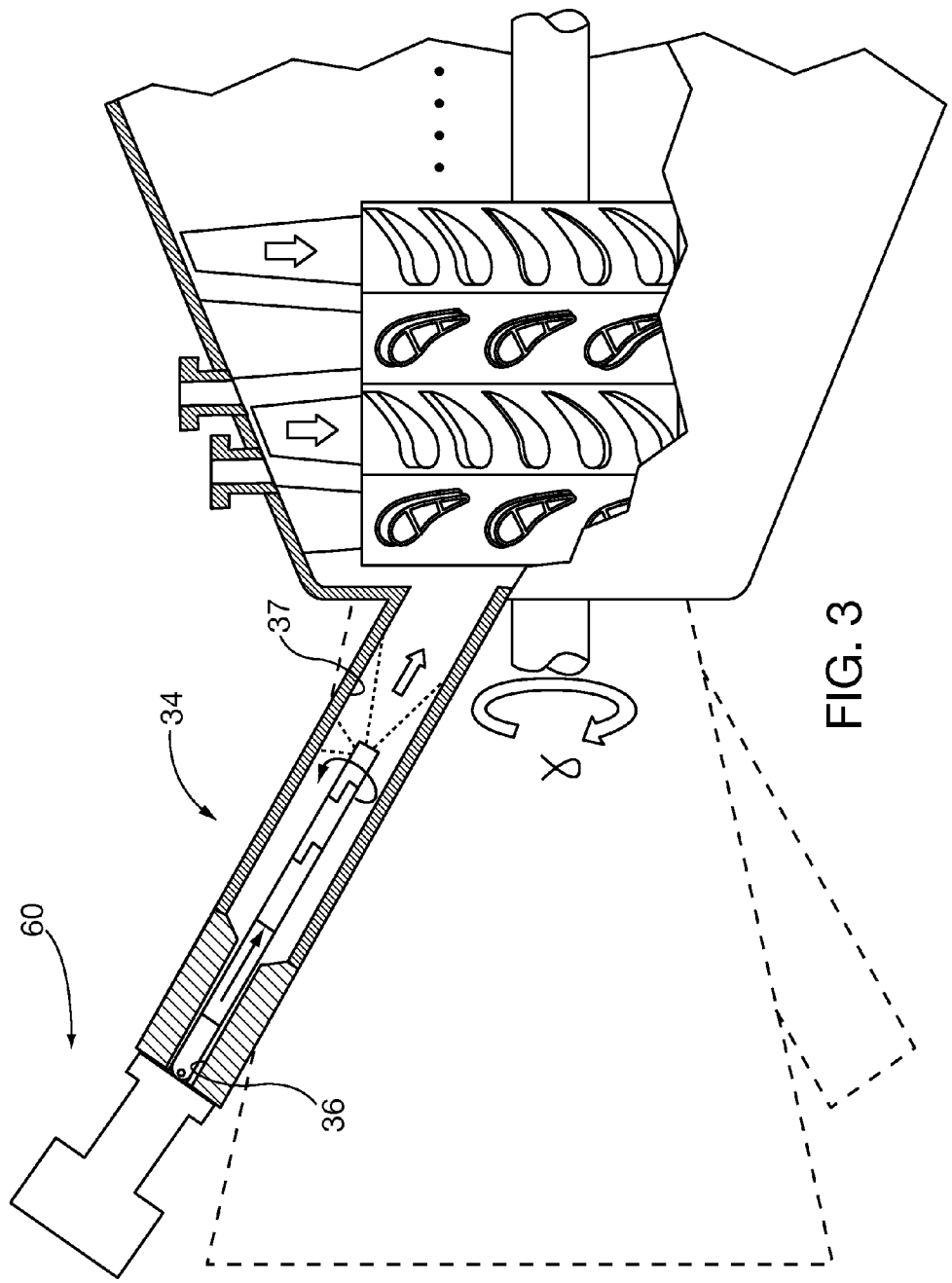
FIG. 3 is partial cross sectional schematic view of a known gas turbine performing an inspection of a combustor internal components with the inspection system of FIG. 2.
Figure 4:
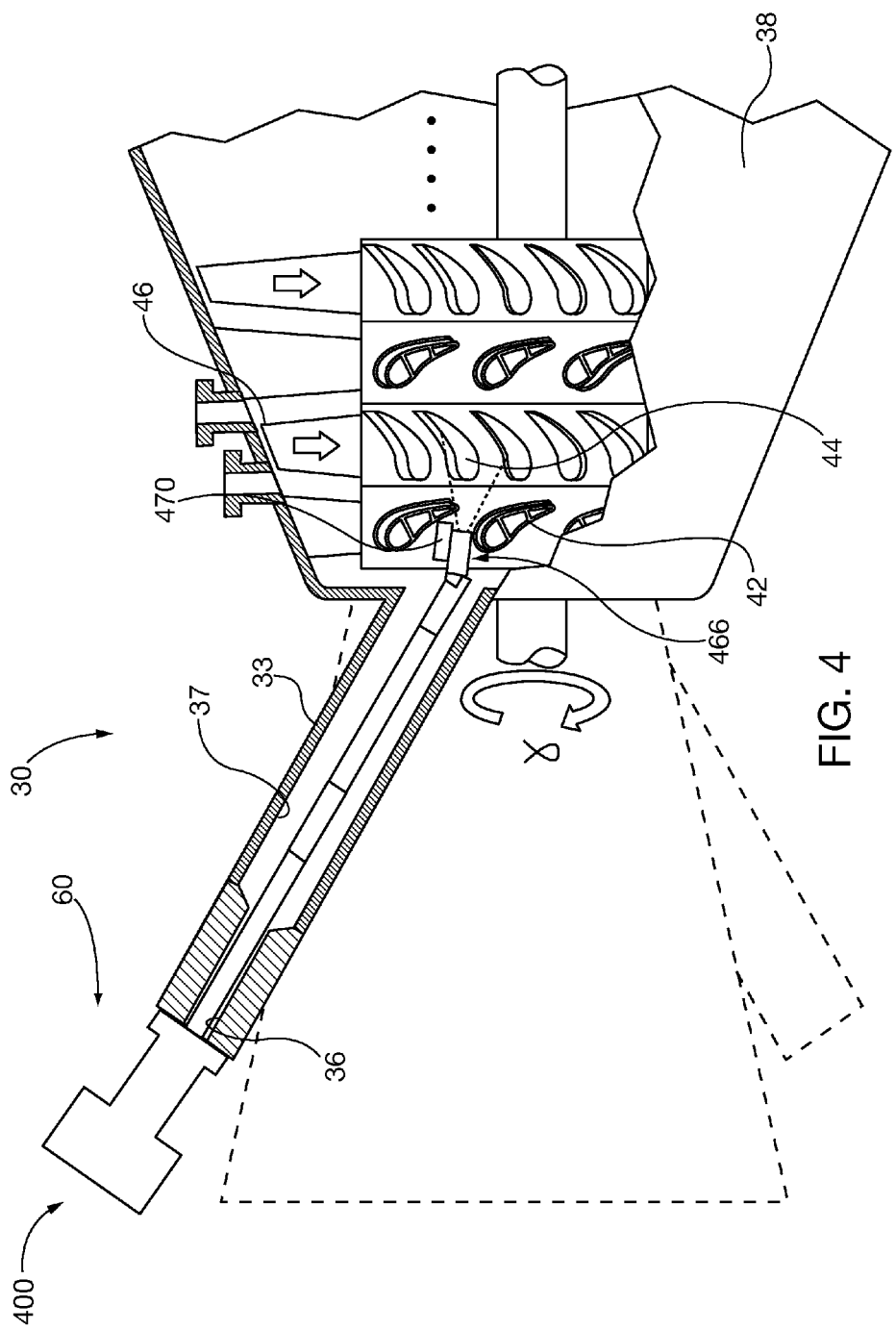
FIG. 4 is partial cross sectional schematic view of a known gas turbine performing a surface profile relative dimensional scanning inspection of a Row 1 turbine blade leading edge surface with the laser profilometer scanning inspection system of the present invention.

FIGS. 2-4 show inspection of an off-line gas turbine by insertion (FIG. 2) of an articulated inspection scope embodiment 60 into a combustor nozzle port 36 that functions as an inspection port. For maneuvering clearance of the scope 60 about the confines of a gas turbine installation, inspection scope 60 has a folding knuckle, so that the scope can be folded into a generally L-shape profile about half as long as an elongated scope. Once the 60 is positioned within the inspection port 36, the knuckle is straightened, as shown in FIG. 3. After the inspection scope 60 is affixed to the inspection port 36, it may be utilized to inspect to combustor and transition internal components by rotating and extending its inspection head 88, 88' or 466. In FIG. 4, as the laser profilometer scanning system embodiment scope 60 with attached laser profilometer head 466, subsequently described in greater detail herein with reference to FIGS. 27-37, is further extended into the inspection port 36, surface profile relative dimensional data and optional images of the combustion section transition inner surface 37, the downstream turbine section 38 vanes 42 and the blades 44 are acquired.

Figure 5:
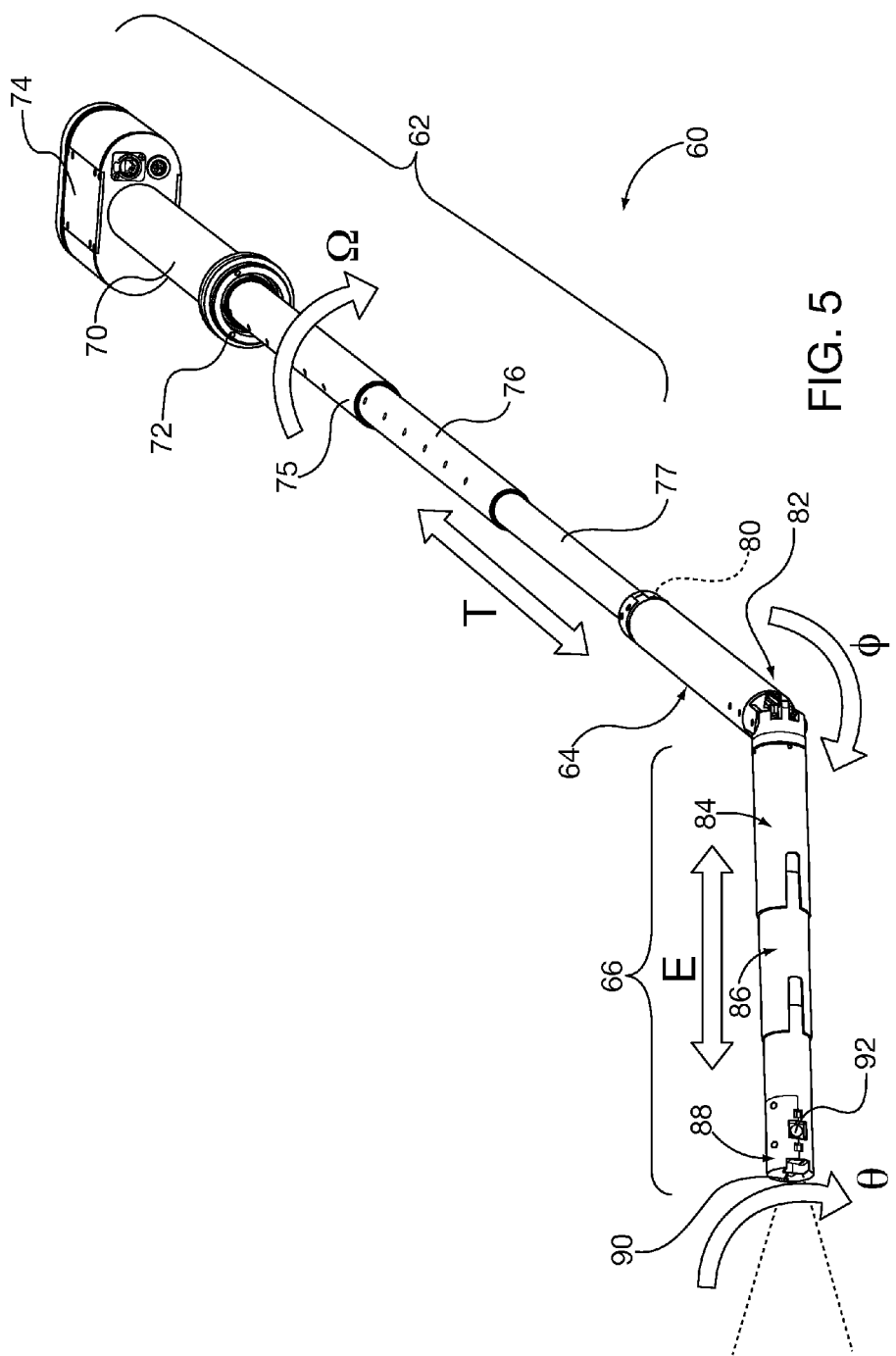
FIG. 5 is a perspective schematic view of the optical camera inspection system of the embodiment of FIG. 2, showing the inspection scope available degrees of motion $\Omega$, T, $\Phi$, E and $\theta$, which inspection scope is also used in conjunction with the laser profilometer scanning inspection system of FIG. 4.

Referring to FIG. 5, the inspection scope 60 has three main component sections: extension tube section 62 (see FIGS. 5-9); motor can 64 (FIGS. 5, 10-12); and camera tip 66 with one of several available optional inspection heads 88, 88' or 466 (FIGS. 5, 12-15, 22-25 and 27-29) that are capable of performing one or more of the following five degrees of motion freedom:

Ω—gross rotation;
T—telescoping extension;
Φ—camera head articulation;
E—camera head tip extension; and
θ camera head rotate/pan.

Depending upon the specific inspection application (i.e., visual inspection only, 3-D scanning or surface profile dimensional inspection) not all degrees of motion freedom are necessarily utilized in any described embodiment. For example, in connection with the dimensional profile scanning embodiments camera head tip extension E is optional, in which case those extension portions are not necessarily installed on the scope 60.

The extension tube section 52 has a mounting tube 70 and mounting collar 72 that are attached to an inspection port, such as the combustor nozzle port 36. Motor housing 74 is attached to the opposite end of mounting tube 70 distal the mounting collar 72 and houses the servo motors necessary to perform the Ω and T degrees of motion. Three telescoping tubes 75-77 collapse into the mounting tube 70 for providing the T directional motion.

Figure 6:
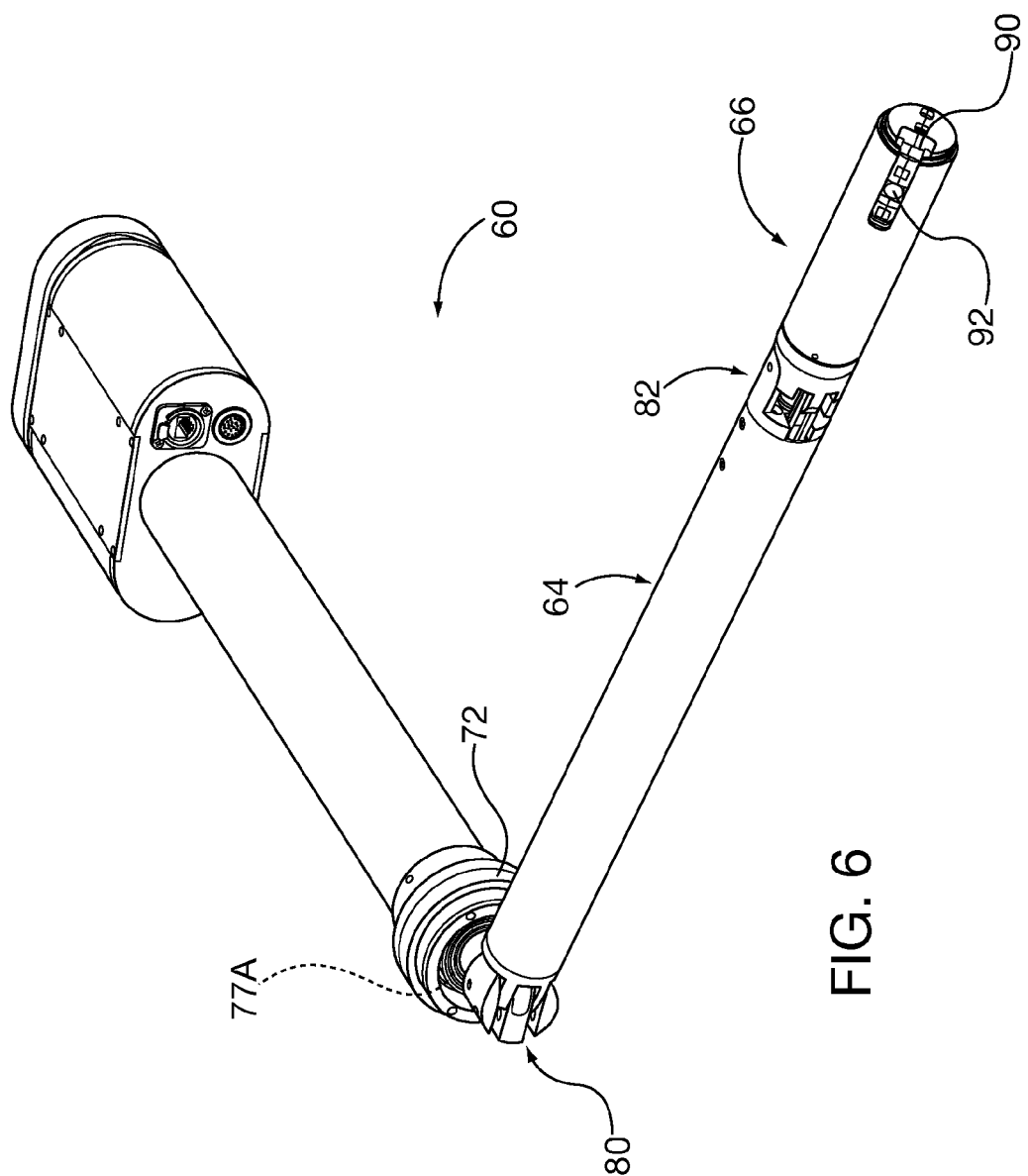
FIG. 6 is a perspective schematic view of the optical camera inspection system of FIG. 5, in the folded insertion position of FIG. 2.
Figure 7:
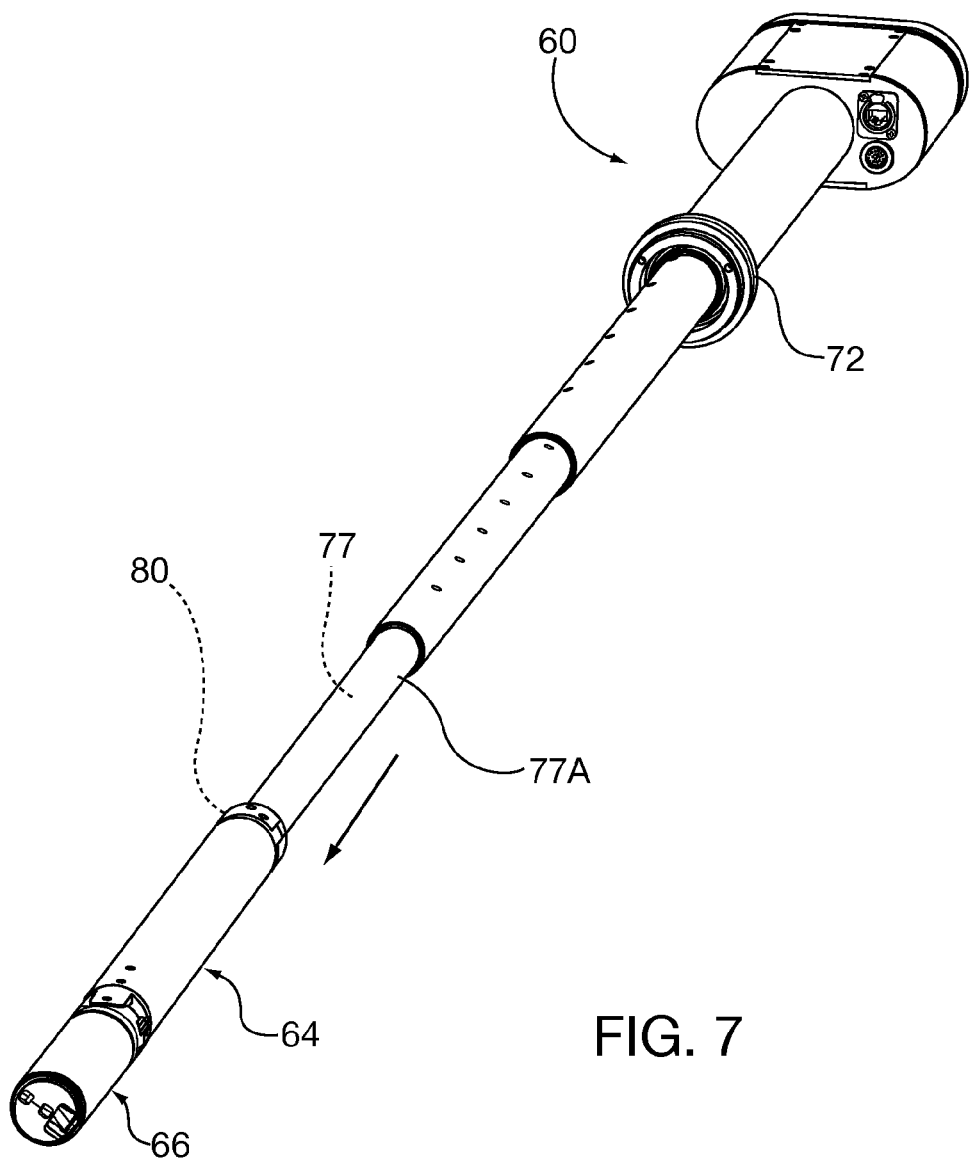
FIG. 7 is a perspective schematic view of the optical camera inspection system of FIG. 5, in the locked inspection position of FIG. 3.

As shown in FIGS. 6 and 7, spring loaded locking knuckle 80 enables the entire inspection scope 60 to fold for compact maneuvering about the turbine 30, as shown in FIG. 2 and described above. Locking sleeve 77A slides over telescoping tube 77 and restrains knuckle 80 therein when the inspection scope 60 is in is locked inspection position as shown in FIG. 7.

As shown in FIG. 5, motor can 64 houses the servo motors necessary to position motorized articulating joint 82 that provides the Φ degree of motion, the camera head 66 head extension motion E via the camera head telescoping extensions 84, 86, and the camera head 88 rotate/pan degree of motion θ. The camera head 88 includes camera ports 90, 92 for respective axial and lateral fields of view (FOV).

Figure 8:
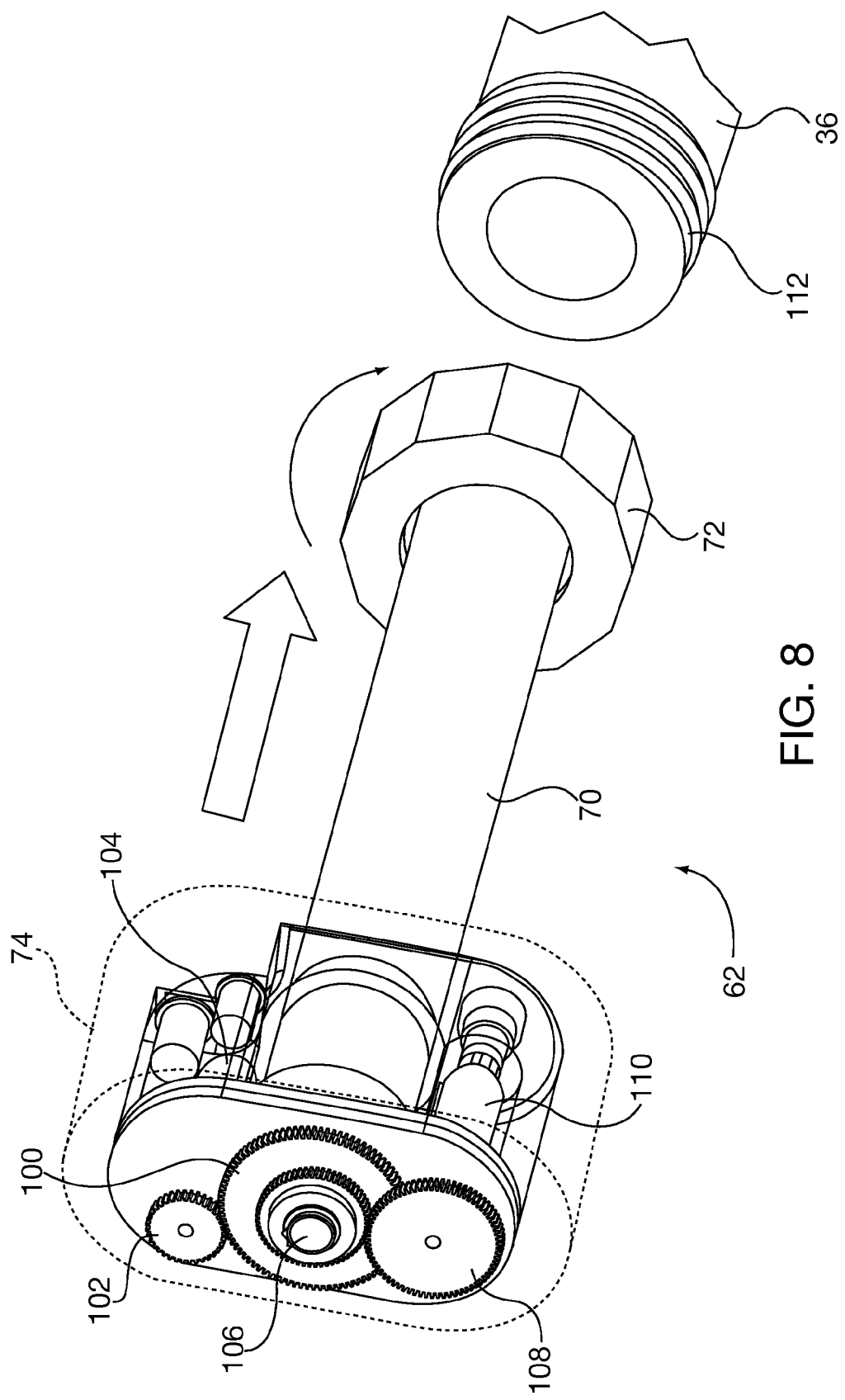
FIG. 8 is a perspective schematic view of the extension tube mechanism portion of the optical camera inspection system of FIG. 5, showing the $\Omega$ and T degrees of motion.
Figure 9:
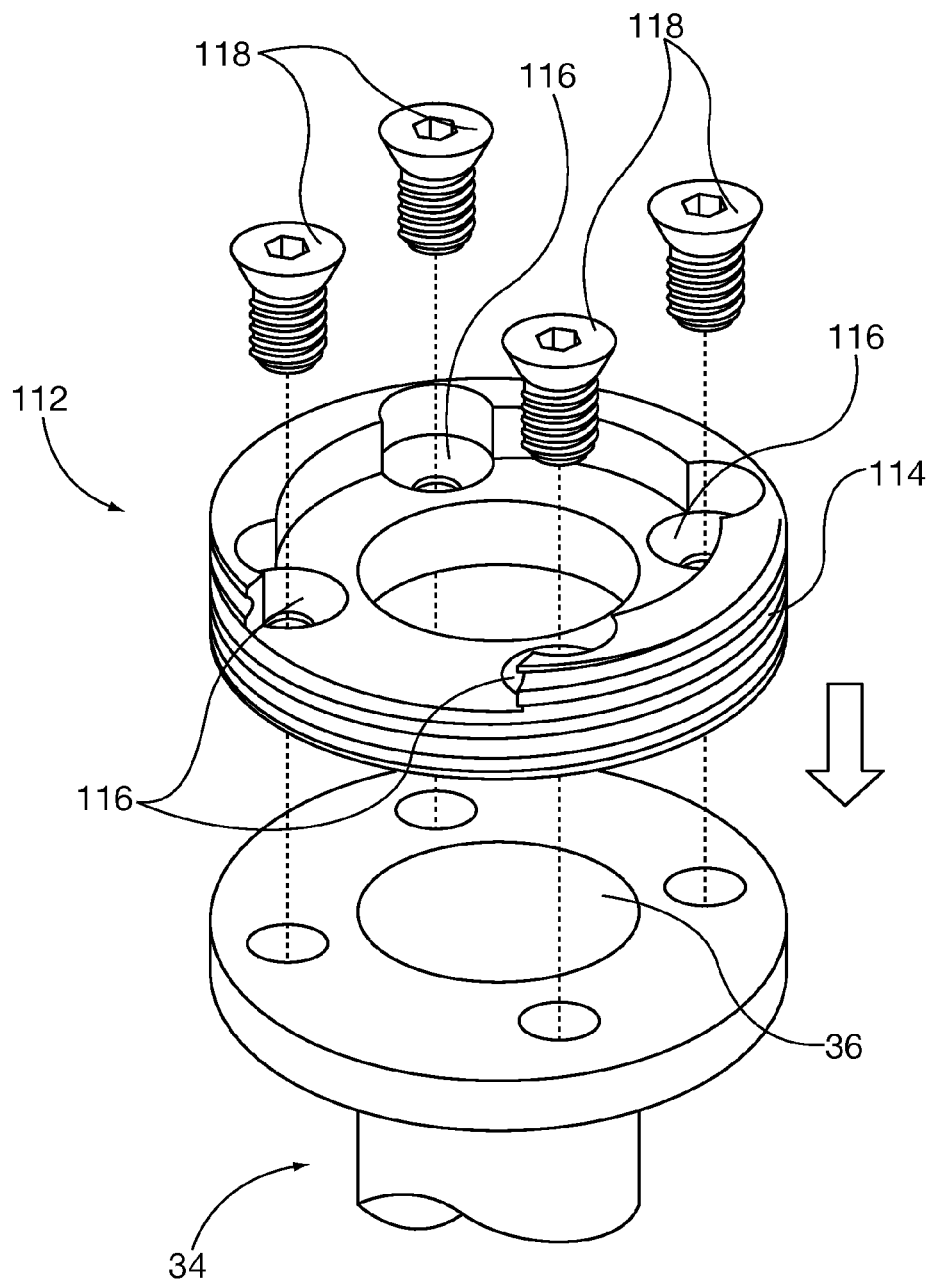
FIG. 9 is a schematic perspective view of an adapter ring of the present invention being attached to a turbine inspection port.
Figure 12:
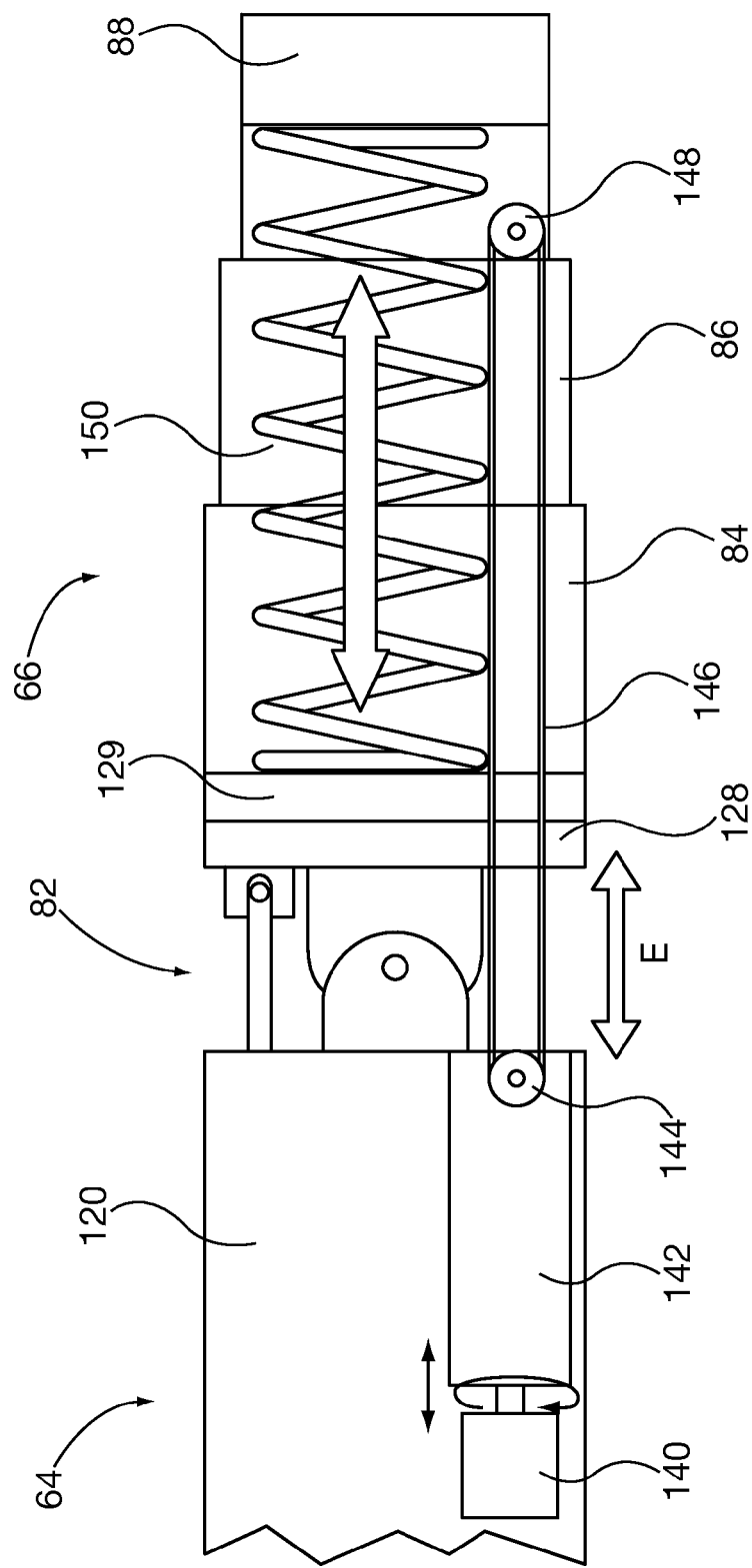
FIG. 12 is a schematic elevational view of a camera head extension mechanism of the optical camera inspection system of FIG. 5, showing the E degree of motion.

FIG. 8 is a detailed view of the motor housing 74, showing two coaxially nested, independently driven large and small diameter gears in the rotation hub 100. Rotate drive gear 102 is driven by the rotate servo motor 104, for effectuating the Ω motion by rotating the larger diameter gear in the rotation hub 100. Telescope extension drive screw 106 is rigidly coupled to the smaller diameter gear in rotation hub 100, that in turn engages the extend drive gear 108. Extend servo motor 110 is responsible for effectuating the T motion by rotating the smaller diameter in the rotating hub 100. Mounting collar 72 attaches to adapter ring 112, that is in turn attached to an inspection port, such as the combustor nozzle inspection port 36. As shown in FIG. 9, the adapter ring includes a plurality of peripheral threads 114 that are engaged with mating internal threads within the collar 72. The adapter ring 112 has mounting holes 116 for receipt of tapered head machine screws 118. The screws 118 may be captively mounted within adapter ring 112. Other configurations of adapter ring or other forms of base that affixes the scope to an inspection port may be substituted for the adapter ring 112.

Referring to FIG. 10, motor can 64 has a motor can housing 120 with a pair of spaced apart ear-like motor can pivots 122. Articulate motion servo motor 124 rotates drive screw 126 that imparts the Φ articulating motion by tipping camera pivoting hub 128. The tipping motion axis 132 is established between camera hub pivot 130 that is rotatively coupled to the motor can pivot 122. Offset link 133 is coupled to drive screw 126 and converts linear motion to rotational motion about tipping motion axis 132.

Motor can housing 120 also contains camera pan/rotate servo motor 134 that imparts the θ degree of motion on camera head 66, as shown in FIG. 11. Servo motor 134 drives bevel gear train 136, which in turn includes the driven bevel gear that is rotatively captured within camera pivoting hub 128, for rotating in turn the rotating hub 129. The rotating hub 129 is rigidly coupled to the camera head telescoping extension 84. Camera tip telescoping extensions 84 and 86 are extended and retracted in the E motion degree by extension servo motor 140 that in turn engages linear drive screw 142. The drive screw 142 includes drive pulley 144, over which passes tensioned cable 146. Slave pulley 148 is attached to camera head 88 and is coupled to cable 146. Coil spring 150 is interposed between camera head 88 and rotating hub 129, and biases them away from each other, thereby tensioning cable 146. It follows that selective translation of the drive screw 142 by the extension servo motor 140 moves the camera head 88 to the left and right in the figure (motion E).

Figure 13:
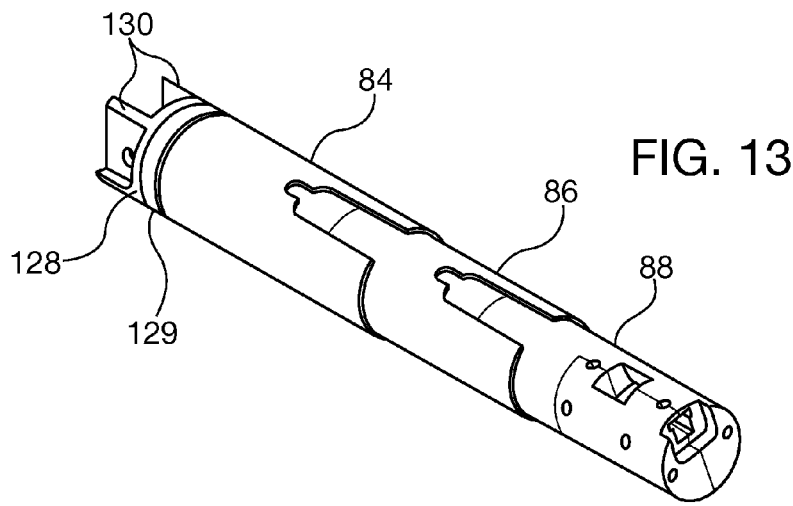
FIG. 13 is a schematic perspective view of the camera head of the optical camera inspection system of FIG. 5.
Figure 14:
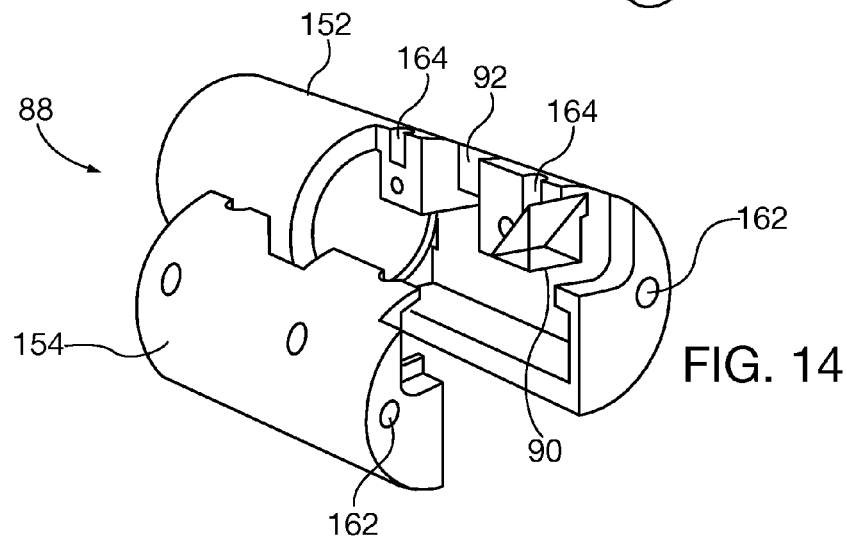
FIG. 14 is a schematic exploded perspective view of a camera head of the optical camera inspection system of FIG. 5.
Figure 15:
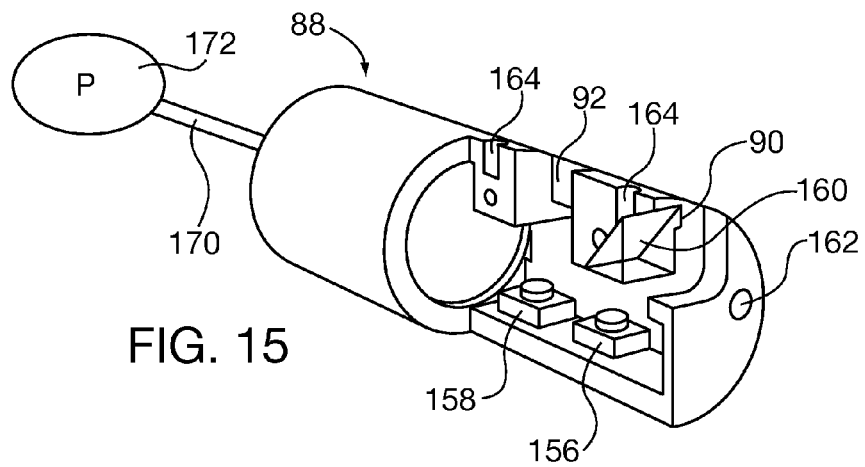
FIG. 15 is a schematic partial assembly perspective view of the camera head of FIG. 14.

FIGS. 13-15 show the optional visual camera head 88 configuration that has a clamshell construction with camera head housing 152 and selectively removable cover 154. Camera 156 has a field of view (FOV) through "camera 1" port 90, extending along the central axis of the camera head 88. Camera 158 has a field of view (FOV) through "camera 2" port 92, extending laterally, or normal to the central axis of the camera head 88. Camera 156 generates its image through prism 160. Cameras 156, 158 are known auto-focusing USB cameras of the type routinely used with personal computers. Light emitting diodes (LEDs) 162 and 164 provide illumination for the cameras 156, 158 during internal inspection of power generation machinery. One or two cameras having different resolution and focus properties may be substituted for auto-focusing USB cameras. Similarly the camera head illumination system may employ LEDs or other illumination sources of desired output intensity or other characteristics, including by way of non-limiting example steady-state or strobe illumination, variable or dimmable intensity outputs.

Three-Dimensional Scanning Camera Inspection System

Figure 21:
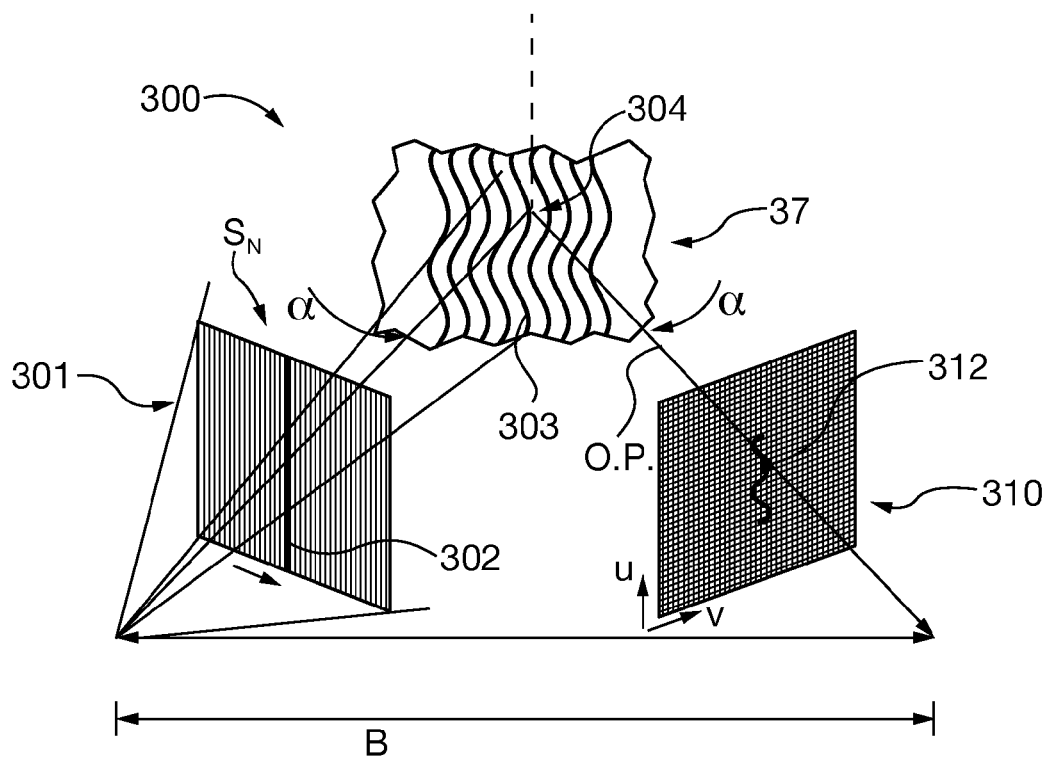
FIG. 21 is a perspective schematic view showing the operational principles of non-contact 3D dimensional scanning performed by the inspection system of the present invention.
Figure 24:
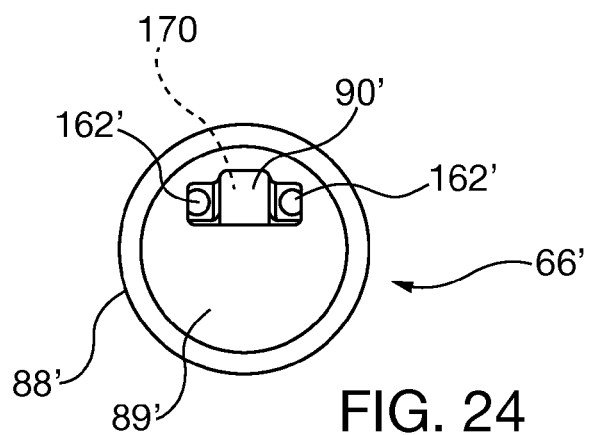
FIG. 24 is a schematic elevational view of the camera head distal tip of the inspection system of FIG. 22.

The optional 3D scanning camera inspection system 300 configuration of with the inspection scope 60 measures the three-dimensional shape of an internal component within a turbine, such as a gas turbine transition 37, without physical contact. Referring to FIG. 21, component shape measurement is performed with a 3D scanner 300 system, by applying known principles of projected light patterns generated by a stripe projector 301 having a two dimensional array $S_N$ of projected stripes 302 and a scanning camera 310 that has a u×v pixel matrix. Projecting a narrow band of light $S_N$ with the projector 301 onto a three-dimensionally shaped surface, such as transition 37, produces a line of illumination 303 that appears distorted from other perspectives than that of the projector 301. For example, line of illumination 303 illuminates object pixel 304 on the shaped surface of transition 37 and its reflection is captured by the matrix camera 310 as camera pixel 312. The series of corresponding camera pixels that capture the reflection is used for an exact geometric reconstruction of the surface shape and can be performed using known commercially available hardware and reconstruction software. For example, in FIG. 21 the three dimensional shape of the line of object pixels 304 along illumination line 303 is determined by the positions of the corresponding captured image of camera pixels 312, the triangulation base distance B and the angle α of incidence and reflection along the optical path (O.P.).

The optional 3D scanning system 300 camera inspection scope configuration substitutes alternative embodiment motor can 64', camera tip or head 66' and articulated joint 82' (with related drive) shown in FIGS. 22-25 for the motor can 64, tip or head 66 and articulation joint 82 (with related drive) that are described in prior FIGS. 10-15. Camera head 66' is coupled to a camera hub 128', which forms the distal end of articulation joint 82'. Camera hub 128' is pivotally coupled to respective distal ends of a pair of parallel links 131' at joint 130'. The proximal ends of links 131' are pivotally coupled to the motor can pivots 122' for mechanical coupling of the motor can 64' and camera tip or head 66'.

Figure 23:
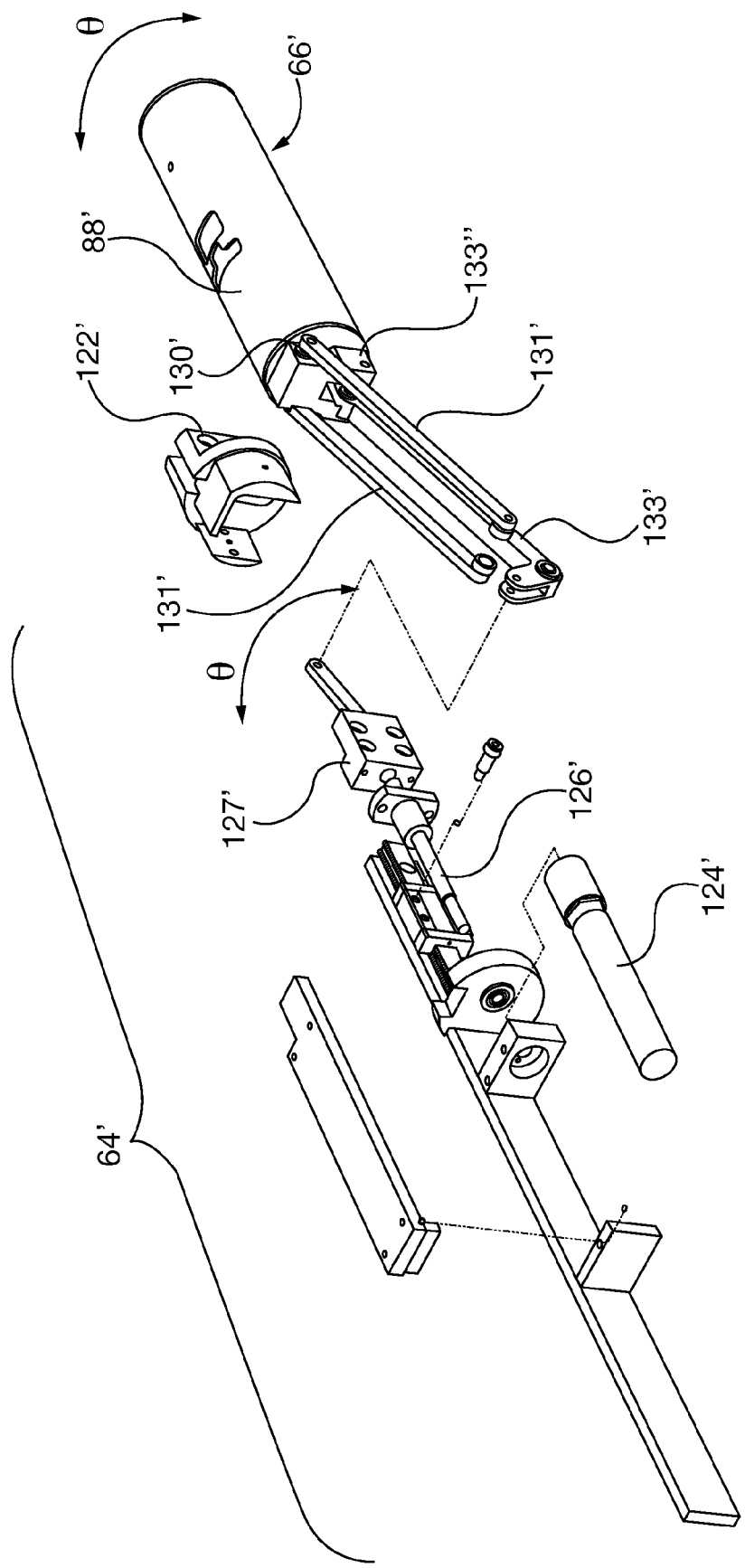
FIG. 23 is an exploded schematic view of the camera head articulation joint mechanism of the inspection system of FIG. 22.

In order to drive the arcuate range of motion Φ, a modified version of the previously described inspection scope system tube section 62 and motor can 64' components upstream of the articulation joint 82' are utilized with the alternative embodiment camera head 66', which are shown in exploded view in FIG. 23. Motor 124' rotates drive screw 126'. Crank assembly 127' converts drive screw 126' rotary motion to arcuate motion Φ. A distal tip of crank assembly 127' is rotatively coupled to a proximal end of offset link 133'. The distal end of offset link 133' is pivotally coupled to the camera hub 128'. It is preferable that the kinematic geometry of the parallel links 131', offset link 133' and their respective relative pivotal connection positions 122', 130' and 133" with respect to the central axes of the motor can 64' and camera head 66' are chosen so that both central axes remain parallel to each other throughout the range of motion Φ. However, other kinematic geometries may be utilized.

FIGS. 22-25 show the camera head 66' that includes camera hub 128', an outer housing 88', and distal tip 89'. Forward visual inspection camera 156' has a field of view (FOV 156') through "camera 1" port 90', extending along the central axis of the camera head 66'. Side viewing visual inspection camera 158' has a field of view (FOV 158') through "camera 2" port 92', extending laterally, or normal to the central axis of the camera head 66'. Camera 156' generates its image through prism 160'. Similarly, camera 158' generates its image along optical path (O.P.) through beam splitter 161' that it shares with scanning camera 310. As will be described in greater detail below cameras 158' and 310' are utilized in separate respective visual and 3D scanning modes of operation, so sharing a common optical path advantageously reduces internal volume of the camera head 66'. Cameras 156', 158' are known auto-focusing USB cameras of the type routinely used with personal computers. Cameras having different resolution and focus properties may be substituted for auto-focusing USB cameras.

Figure 22:
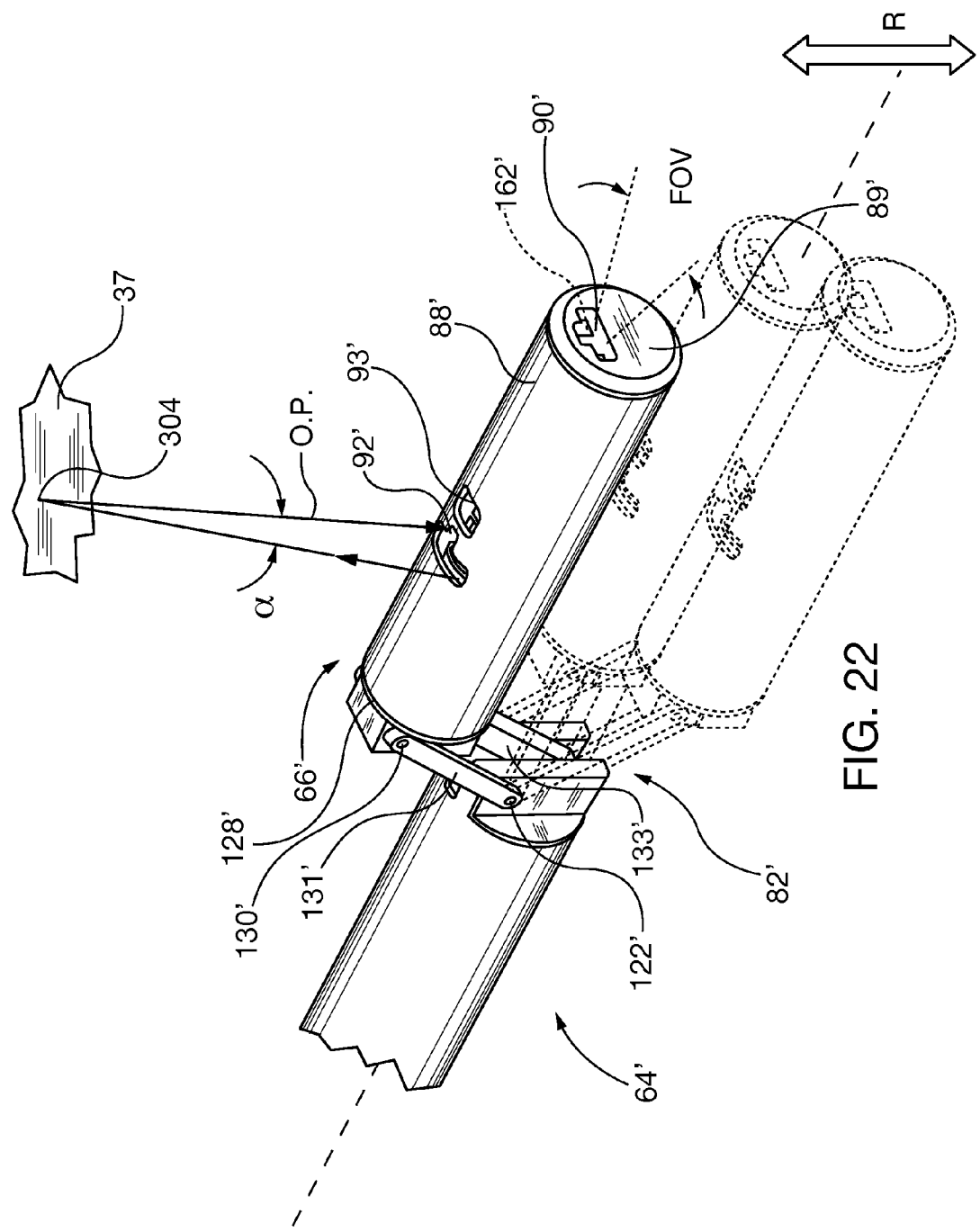
FIG. 22 is a perspective view of the range of motion of a camera head of the non-contact 3D dimensional scanning inspection system of the present invention.

The 3D scanning system 300 components within the camera head 66' comprise the projector 301 and 3D camera 310. Exemplary projectors and 3D cameras are available from XIMEA Corp. of Golden, Colo., USA. The projector 301 projects a light beam along an optical path through prism 305 that exits the camera head outer housing 88' through aperture 92'. In an exemplary embodiment of the present invention, the projector 301 and the 3D camera 310 are oriented so that incident projected light converges with the camera 310 O.P. at an angle α of 10 degrees and an optical path length of 3.94 inches (100 mm). Incident and convergent light pass through optical port 92' that is formed within the housing 88'. In order to aid alignment of the camera head at the desired distance of 100 mm from an inspection surface, such as transition 37, a diode laser 320, that is in visual communication with the laser port 93' formed within the camera housing 88', projects a focus dot 321 on the transition 37 surface. The desired O.P. distance of 100 mm is achieved when the laser dot is in focus of camera 310. The camera head 66'is aligned relative to the transition surface 37 by articulating the articulation joint mechanism 82' articulation angle Φ. This in turn translates the camera head 66' radially relative to the scope 60 central axis along the direction R, as shown in FIGS. 4 and 22. The inspection system may automatically orient the camera head 66' along the radial direction R through a known feedback loop until the laser spot 321 is focused. Upon achieving desired laser spot 321 focus, spot projection by laser 320 is ceased prior to commencement of a 3D scanning procedure.

An illumination system, shown comprising pairs of light emitting diodes (LEDs lights 162' and 164'are respectively mounted co-axial and transverse with the camera head 66'central axis. They provide illumination for the cameras 156', 158' during internal visual inspection of power generation machinery. The LED lights 162' and 164' may be oriented in any desired position relative to the camera head 66' central axis The camera head illumination system may employ LEDs or other illumination sources of desired output intensity or other characteristics, including by way of non-limiting example steady-state or strobe illumination, variable or dimmable intensity outputs. The illumination system is not utilized when performing dimensional scans with the 3D scanning system 300 or when projecting a focusing spot 321 with the laser 320. Thus, if desired, the illumination system LED lights 162', 164' and laser 320 may share a common power source and lighting control system (see, e.g., FIG. 26).

Laser Profilometer Surface Profile Inspection System

The laser profilometer inspection system 400 configuration, utilizing the scope 60, scans and gathers measures relative surface height profile dimensional data of an internal component within a power generation machine, such as a gas turbine engine 30 transition 37, vane 42, blade 44, or blade gap G without physical contact, for subsequent image processing and relative dimensional indication. Referring to FIGS. 27-30, component surface profile scanning and measurement of an area of interest of an outer surface of an exemplary turbine section vane 42 is performed with a laser profilometer 410 that is affixed to a profilometer head 466 on the distal end of the inspection scope 60. The profilometer 410 includes a scanning face 411, incorporating a laser projector 412 that projects a two-dimensional (2-D) laser stripe 414 having an angular field of view (FOV) α spanning the vane 42 surface along width X and vertically spaced by distance Z. The projected laser stripe 414 reflects off the surface 42 as a reflected laser light pattern 416, and deflects in correlation to the relative height along the surface. The profilometer scanning face 411 has a reflected laser light receiving 2-D matrix-like sensor array 418. A varying component surface profile along the projected laser stripe 414 will cause the reflected light 416 to strike the sensor array 418 at different sensor pixel locations. The series of corresponding sensor 418 pixels that capture the reflection is used for reconstruction of the surface 42 profile. The profilometer 410 is a commercially available scanCONTROL brand product of Micro-Epsilon USA of Raleigh, N.C., USA.

The surface profilometer scanning system 400 configuration embodiment of FIGS. 27-38 utilizes the inspection scope 60 hardware and motion control system up to the articulating joint 82 and substitutes alternative structural embodiment laser profilometer head 466 for the cameral head 66. While the embodiment of laser profilometer head 466 shown in FIG. 27 does not have provision for extension motion E, such extension feature can be added to the inspection system 400. The profilometer head 466 is coupled to the respective pivoting and rotation hubs 128, 129 in order to impart the selective Φ and θ ranges of motion of the profilometer 410 field of view (FOV). The laser profilometer 410 is affixed to the inspection scope 60 hub 129 by profilometer bracket 467. The profilometer bracket 467 includes side plates that are fastened to flanking sides of the profilometer 410. One of the side plates also provides a mounting surface for a camera and/or illumination source housing 470 that is generally oriented parallel to the inspection scope 60 central axis and perpendicular to the profilometer scanning face 411.

The camera housing 470 incorporates a visual camera 156 and/or an illumination source 164. The camera 156 is a known auto-focusing USB camera of the type routinely used with personal computers. Cameras having different resolution and focus properties may be substituted for auto-focusing USB camera 156. The illumination system 164 comprises one or more light emitting diodes (LEDs), which provide illumination for the camera 156 during internal visual inspection of power generation machinery. The LED light or lights 164 may be oriented in any desired position relative to the profilometer head 466 scanning face 411. The camera head illumination system may employ LEDs or other illumination sources of desired output intensity or other characteristics, including by way of non-limiting example steady-state or strobe illumination, variable or dimmable intensity outputs. The illumination system is not utilized when performing dimensional profile scans with the laser profilometer 410.

Inspection Scope Cooling System

Figure 25:
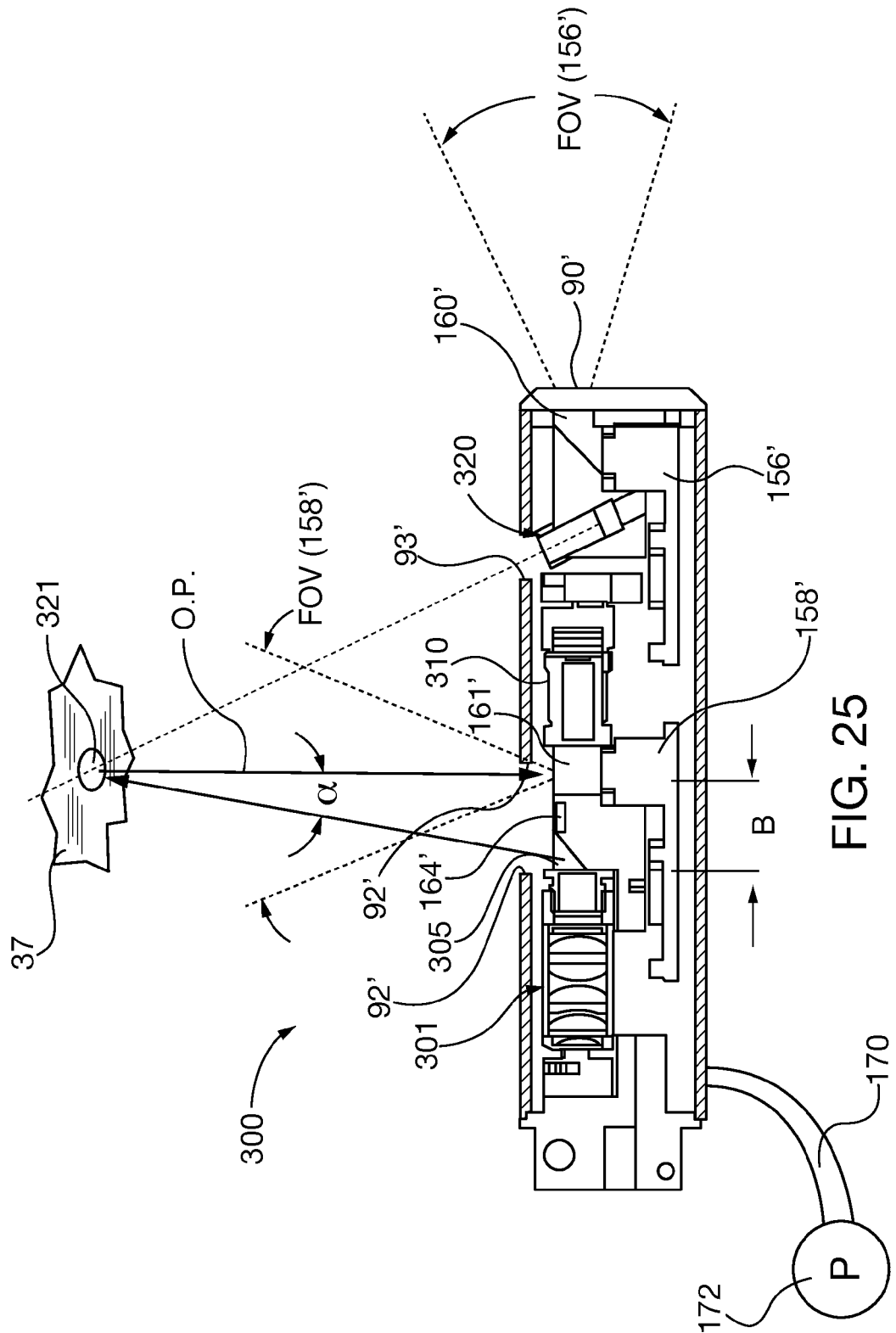
FIG. 25 is an partial axial cross-sectional schematic view of the camera head of the inspection system of FIG. 22.
Figure 27:
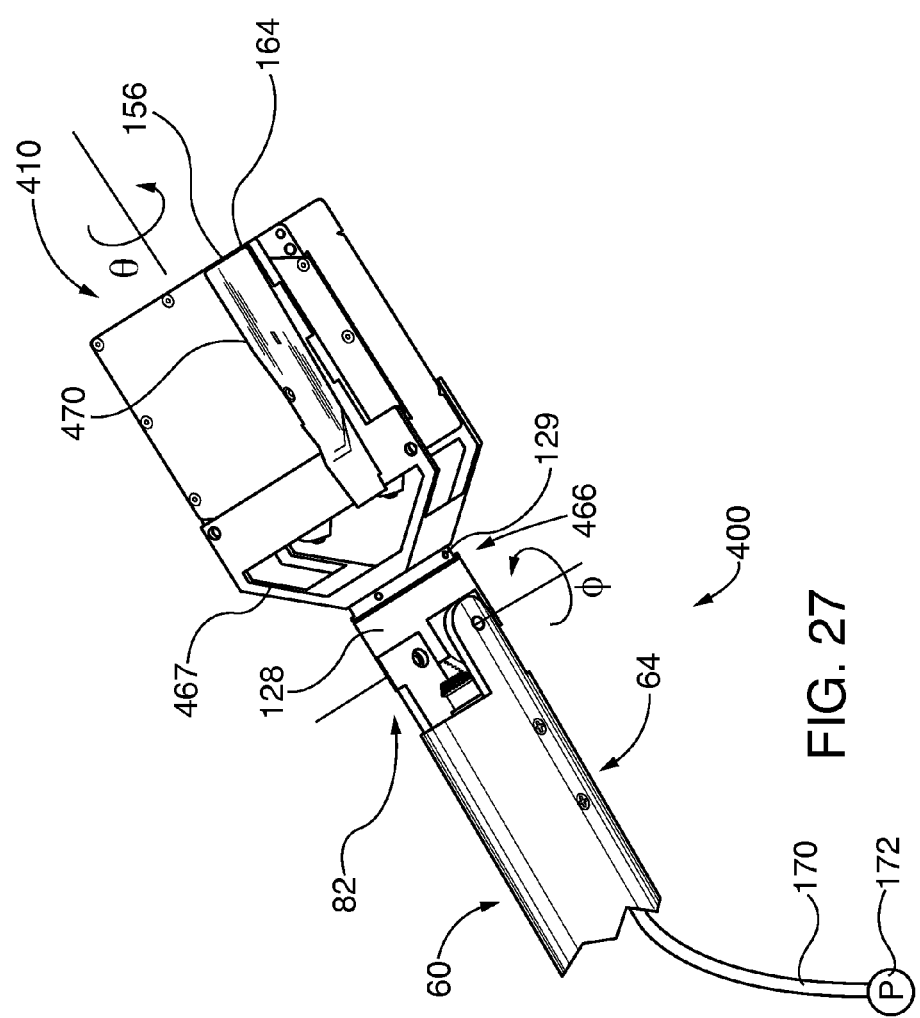
FIG. 27 is a perspective view of the laser profilometer head, including laser profilometer and optional external visual camera, of the non-contact surface profile relative dimensional measurement scanning inspection system of the present invention, including the embodiment of FIG. 4.
Figure 30:
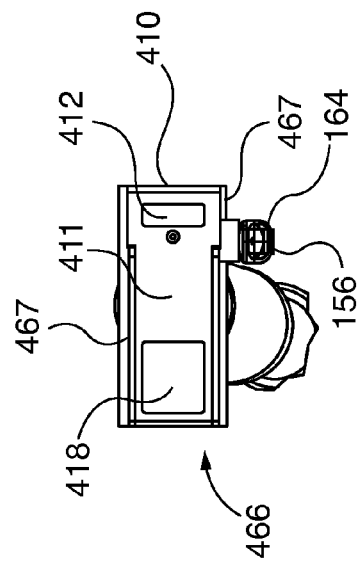
FIG. 30 is a front elevational view of the laser profilometer head, including laser profilometer and optional external visual camera, of FIG. 27.

Inspection scope 60, utilizing any of the camera head embodiments 66, 66' or 466, is optionally and preferably externally cooled by a cooling air line 170 and pressurized cooling air source 172 (e.g., compressed air), schematically shown in the respective embodiments FIGS. 15, 25 and 27. Cooling air passes through the scope 60 to transfer heat away from the instrument, where it exhausts through gaps within the scope outer surface, such as the camera ports 90, 92, 90', 92', the laser port 93', the prisms 160, 160', 164' around the cameras 156, 158, 156', 158', 310' and the LEDs 162, 164, 162', 164' or around the profilometer head 466, in order to cool the laser profilometer 410. Those gaps effectively function as cooling air exhaust ports. Cooling air exhausting the various cooling ports helps transfer heat out of the scope 60 and helps create a thermal barrier around the camera head 88, 88', 466 that is relatively cooler than a not fully cooled turbine 30 internal temperature. In this manner, the inspection scope 60 can be inserted into still hot shut-down turbine many hours before it cools to ambient air temperature. In this manner, inspection can be initiated many hours—and possibly days—earlier than was permissible with known inspection systems. Thus an inspection procedure can be initiated and completed earlier in a turbine service period than was possible in the past, possibly reducing the aggregate maintenance cycle time.

Inspection System Control and Operation

Figure 16:
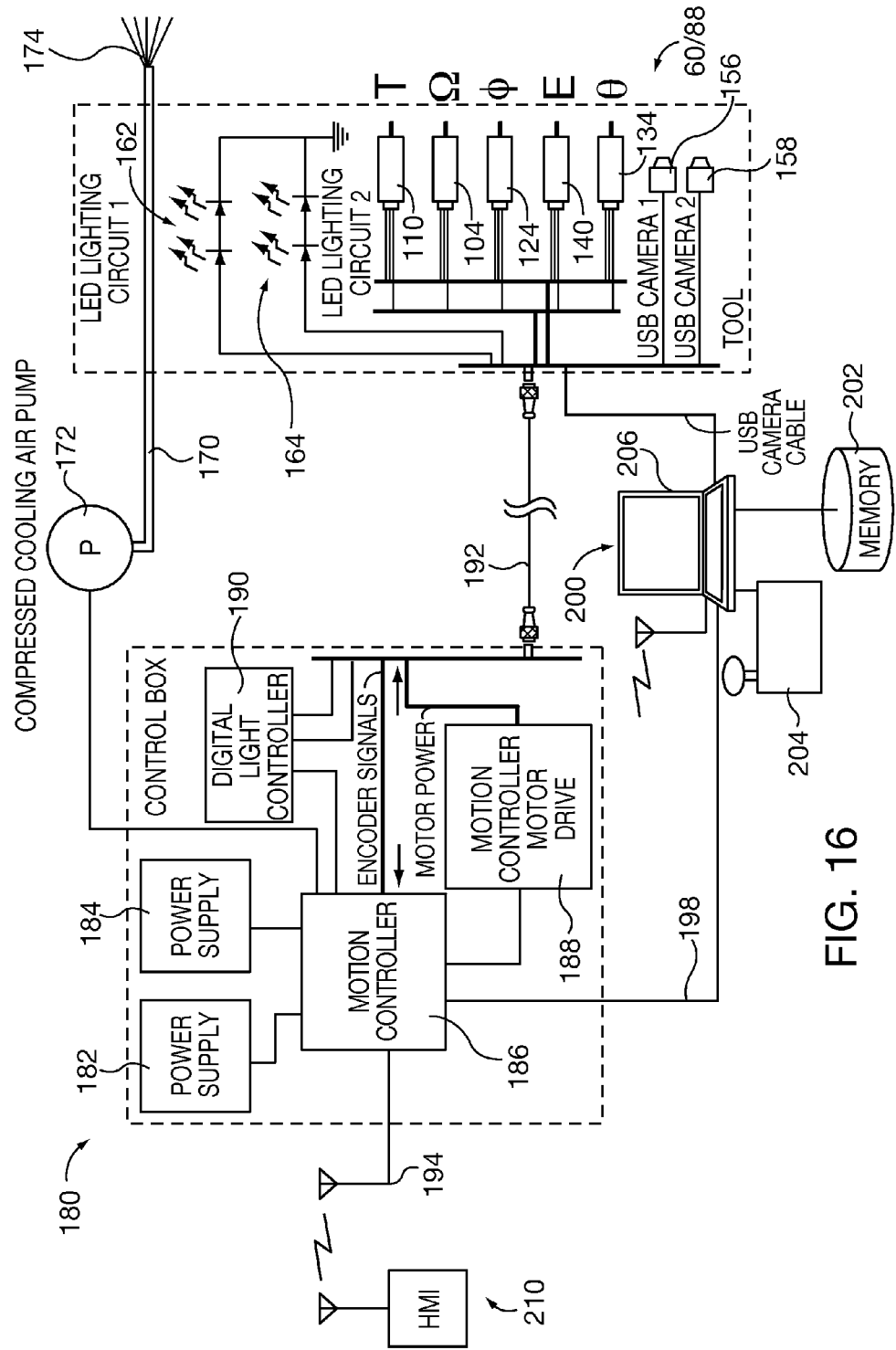
FIG. 16 is a block diagram of the control box and controls system for the optical camera inspection system of FIG. 5.
Figure 26:
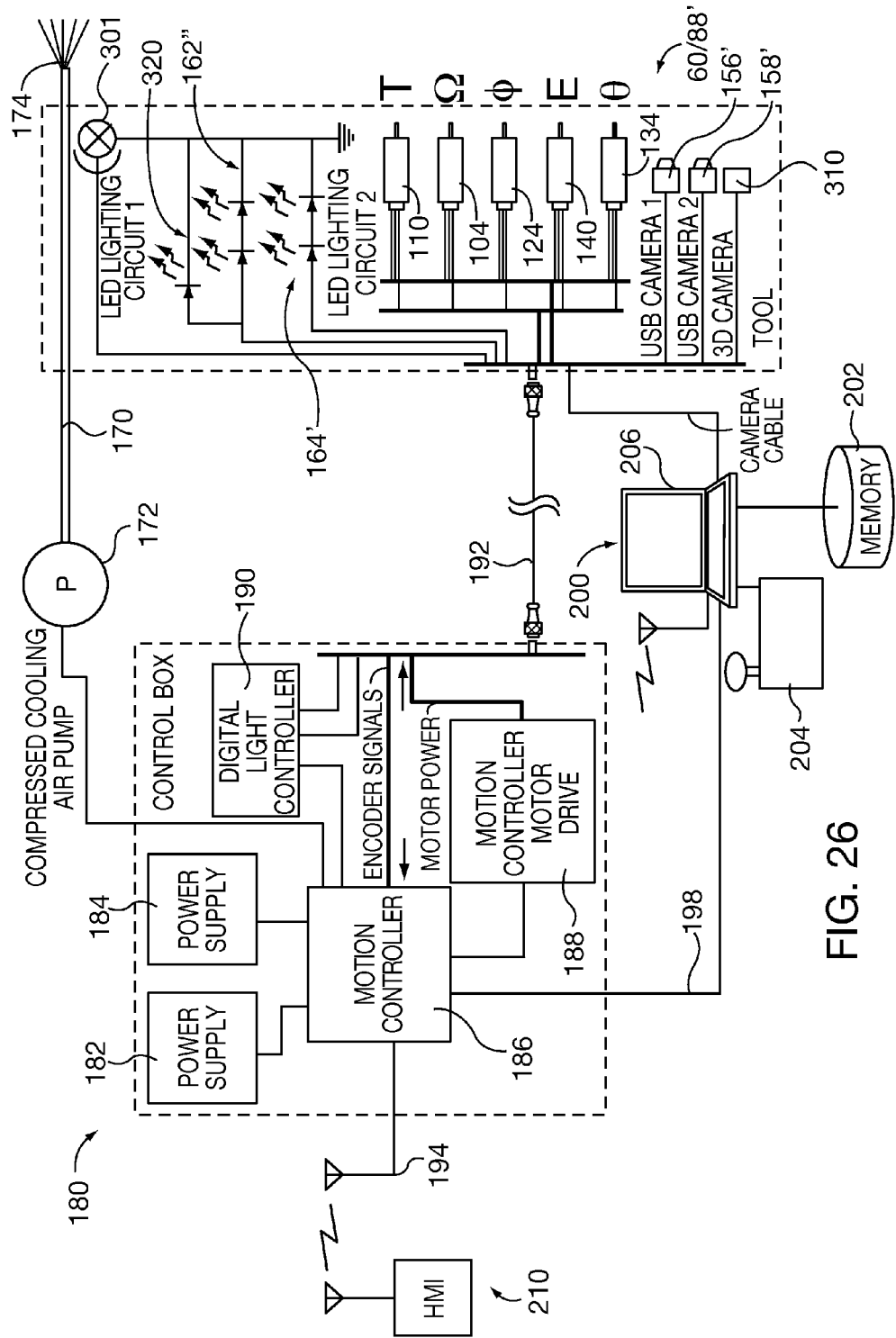
FIG. 26 is a block diagram of the control box and controls system for the optical camera inspection system of FIG. 22.
Figure 31:
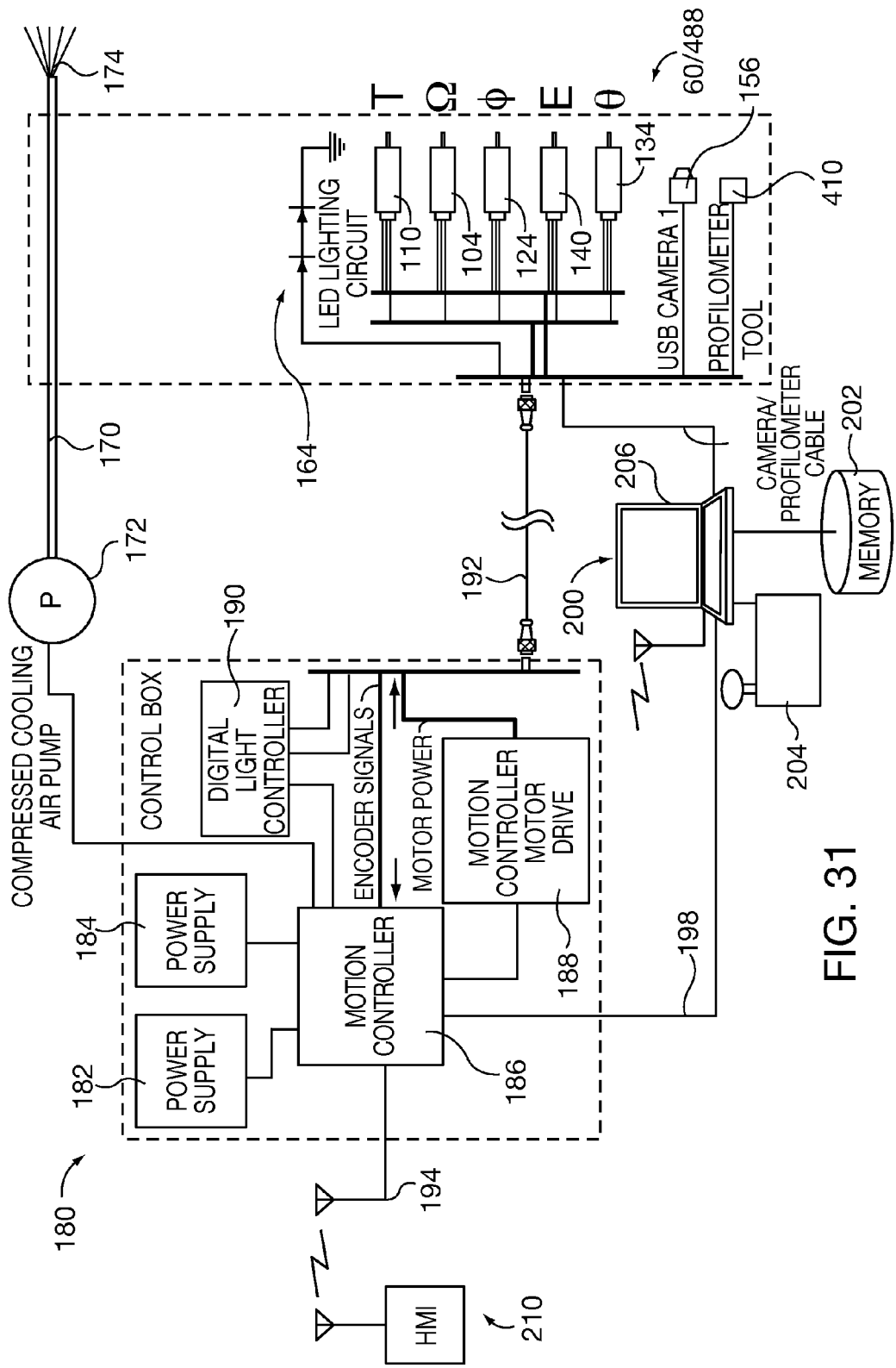
FIG. 31 is a block diagram of the control box and controls system for the inspection system of FIGS. 4 and 27.
Figure 32:
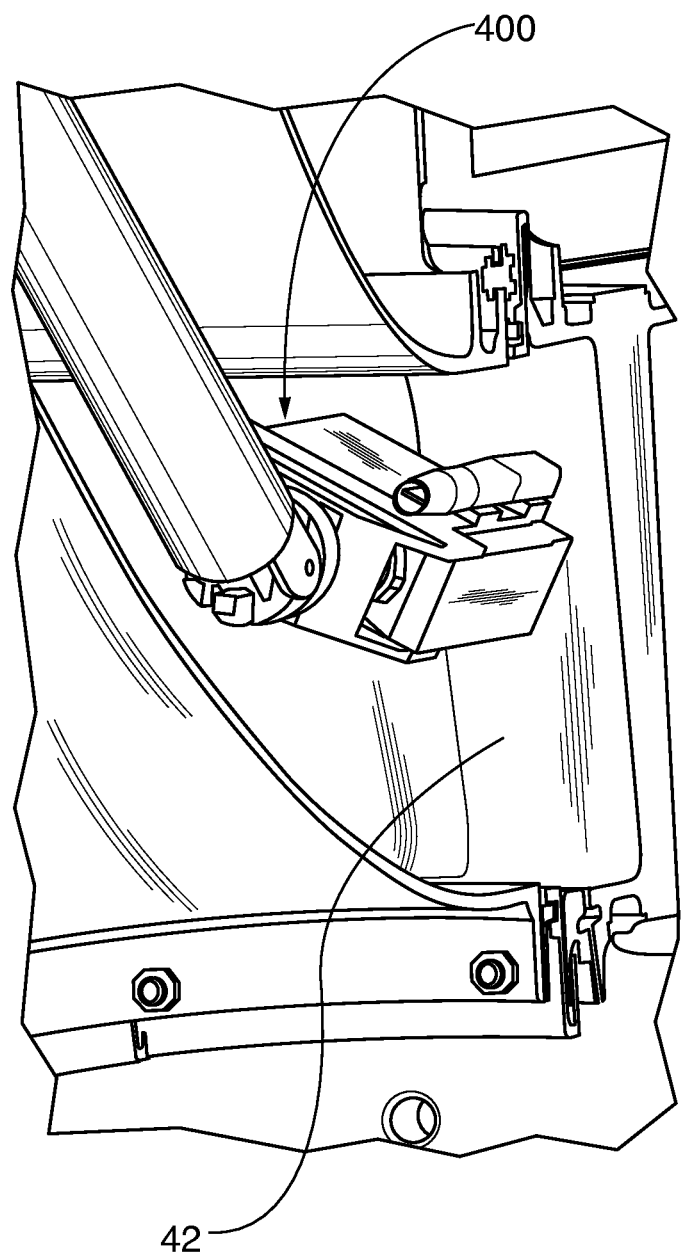
FIG. 32 is a perspective view of the inspection system of FIGS. 4 and 27 obtaining surface profile scan data of a combustion turbine section Row 1 vane.

Inspection scope 60 positioning along it's up to five described degrees of motion are accomplished by energizing any of the five previously described precision motion control servomotors 104 (Ω), 110 (T), 124 (θ), 124 (Φ), and 140 (E). The servomotors have associated encoders that provide motor position information feedback for use by the controller of a known motion control system. FIG. 16 is block diagram of an exemplary motion control system of the present invention that is utilized with the visual camera head 66 of FIGS. 13-15. A corresponding block diagram for the 3-D camera head 66' of FIGS. 21-25 is shown in FIG. 26. Another corresponding block diagram for the dimensional laser profilometer head 466 of FIGS. 27-30 is shown in FIG. 31. In all of the three FIGS. 16, 26 and 31 common components and function have identical numbers and include the following common operational description. The previously described inspection scope 60 hardware, including the distally attached respective inspection head 88, 88' or 466, are designated by dashed line 60/, and is in communication with control box 180, also designated by dashed line, by way of known communication pathways, such as multi-pathway cable 192 and respective camera cables.

Control box 180 includes first and second power supplies 182, 184 for powering motion controller 186 and motion controller motor drive 188. All of components 182-188 are of known design utilized for industrial motion control systems. The motion controller 186 issues commands to the motion controller motor drive 188 for energizing and reversing the inspection scope 60 servo motors 104 (Ω), 110 (T), 124 (θ), 124 (Φ), and 140 (E). For brevity all such motors are collectively referred to as "servo motors". The respective servomotors have associated encoders that generate encoder signals indicative of the scope position within its respective range of motion. For example, the encoder associated with servomotor 104 generates a rotational position signal indicative of the gross rotational position (Ω) of the extension tube portion 62. Position signal information from each encoder is accessed by the motion controller 186. The motion controller 186 correlates respective motor encoder signals with inspection scope 60 spatial position. Digital light controller 190 controls the LEDs 162, 164 or 162', 164',luminal output and on/off (including strobe function, where applicable), the 3D scanning system 300 stripe projector 310 and the focus spot generating laser 320. The digital light controller 190 also communicates with the motion controller 186 and the host controller 200. The motion controller 186 also controls cooling airflow into and through the inspection scope 60, for example flow rate out the cooling port 174.

Motion controller 186 of any of the three embodiments of FIGS. 16, 26 and 31 has an optional wireless communication capability 194. Hardwired data pathway 198, for example, a cable transmitting communications signals in conformity with Ethernet protocol, is in communication with a host controller 200. An exemplary host controller 200 is a personal computer with internal memory capacity and if desired external memory 202. Optionally, the host controller 200 incorporates or integrates the motion controller 186 and/or the digital light controller 190 functions. The host controller computer 200 also controls operation of as well as receives and processes output image data from camera 156/156' (USB Camera 1), camera 158/158' (USB Camera 2), the laser profilometer system 400 USB camera 166, the 3D scanning system camera 310 and the laser profilometer 410.

The image data of the 3D scanning system camera 310 are processed to generate dimensional data respecting the scanned surface, such as that of the transition 37 of FIGS. 4 and 21 using known image processing software. An exemplary 3D scanning image processing software is the "Mesh-Lab" package of open source software that is downloadable via the Internet from the National Research Council of Italy Visual Computing Lab. Another source for exemplary 3D scanning image-processing software is Geomagic of Research Triangle Park, N.C., U.S.A.

The host controller computer 200 may archive or otherwise store raw or processed image data in memory 202. Inspection scope 60 can be positioned under human command and control, such as via joystick 204 and/or HMI viewing/touch screen 206. Respective visual and reconstructed dimensional images from the cameras 156/156', 158/158' and 310 can be viewed by HMI viewing screen 206 or communicated to other image viewing or data processing systems via known communication pathways.

The profile data output of the surface profile profilometer scanning system profilometer 410 are processed to generate profile relative dimensional data respecting the scanned surface, such as that of the transition 37, vane 42, blade 44 or blade tip gap G of FIGS. 4, and 31-37 using known surface profile processing software. Exemplary known surface profile scanning image-processing software is the "scan CONTROL SMART" software package available from Micro-Epsilon USA of Raleigh, N.C., USA that is used in conjunction with its scan CONTROL brand profilometers.

The host controller computer 200 may archive or otherwise store raw or processed surface dimensional image data in memory 202. Inspection scope 60 can be positioned under human command and control, such as via joystick 204 and/or HMI viewing/touch screen 206. Respective visual and reconstructed dimensional images from the cameras 156/156', 158/158', 310, and the profilometer 410 are optionally viewed by HMI viewing screen 206 or communicated to other image viewing or data processing systems via known communication pathways.

Figure 17:
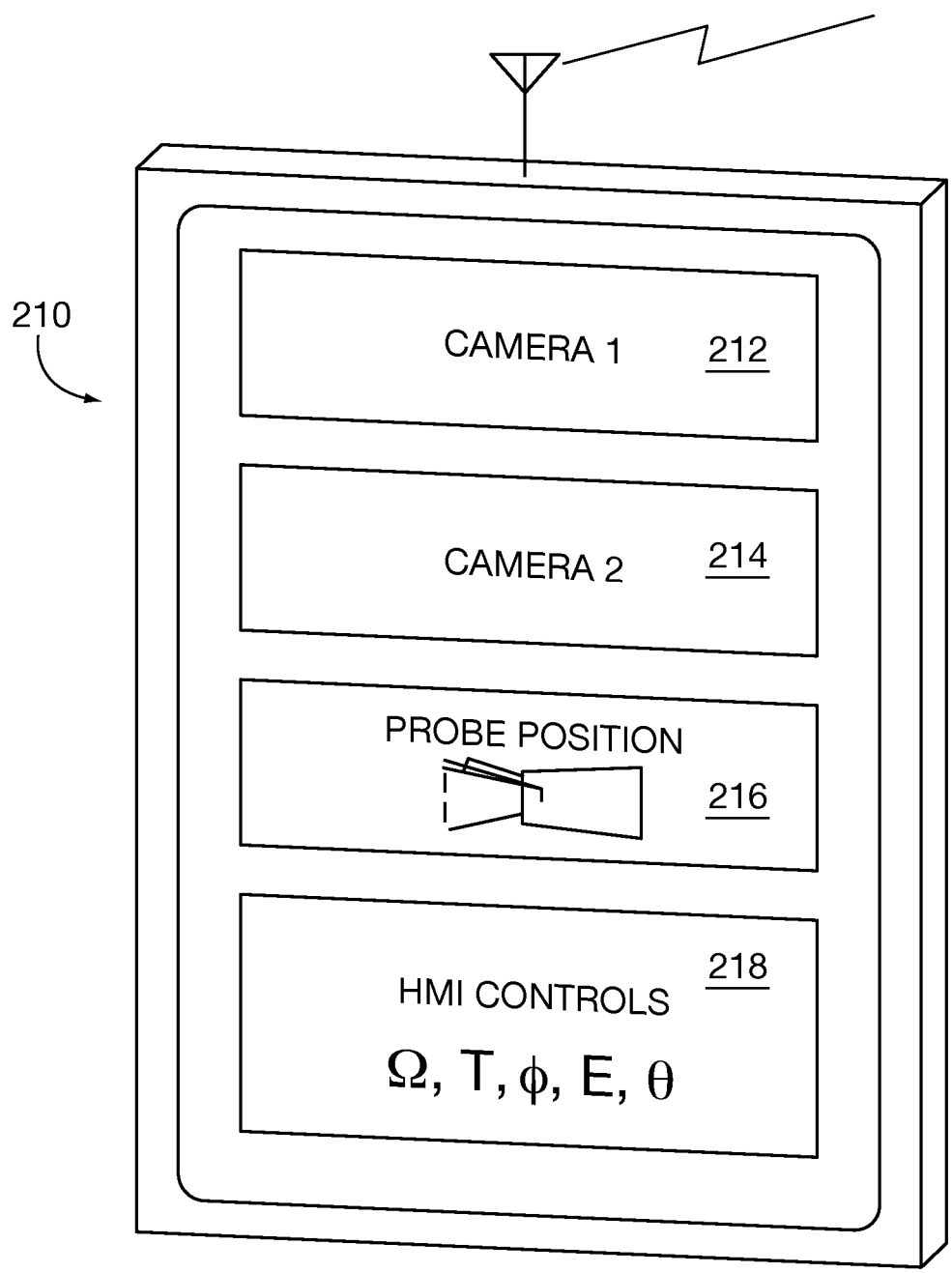
FIG. 17 is a perspective schematic view of an embodiment of a tablet computer human machine interface (HMI) for operator remote monitoring and control of an inspection system described in the present application.

Optionally the computer 200 may have wireless communication capability, for example to communicate with other computers, including for example a tablet computer 210 with HMI, such as for example a tablet computer. FIG. 17 shows an exemplary tablet computer, HMI display screen including Camera 1 image display 212, Camera 2 image display 214, probe position information display 216, and an HMI control interface 218 for manipulating inspection scope 60 positions. The tablet computer 210 may have direct communications capability with the motion controller 186, without the need to communicate through the host controller computer 200.

Blade/Vane Inspection Scope

Figure 18:
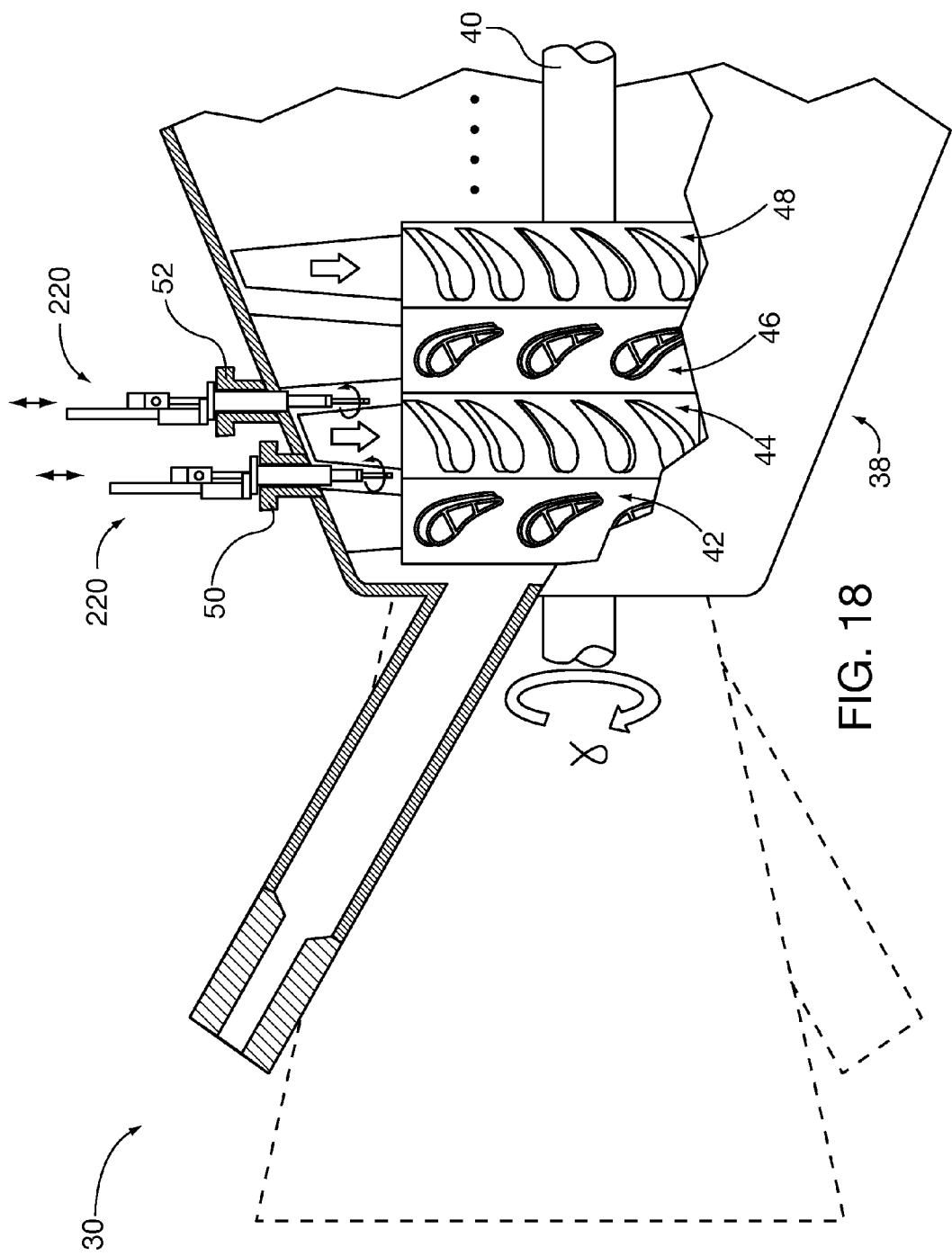
FIG. 18 is a partial cross sectional schematic view of a known gas turbine showing insertion of another optical camera inspection system described in the present application into two separate turbine section rows respective inspection ports.
Figure 19:
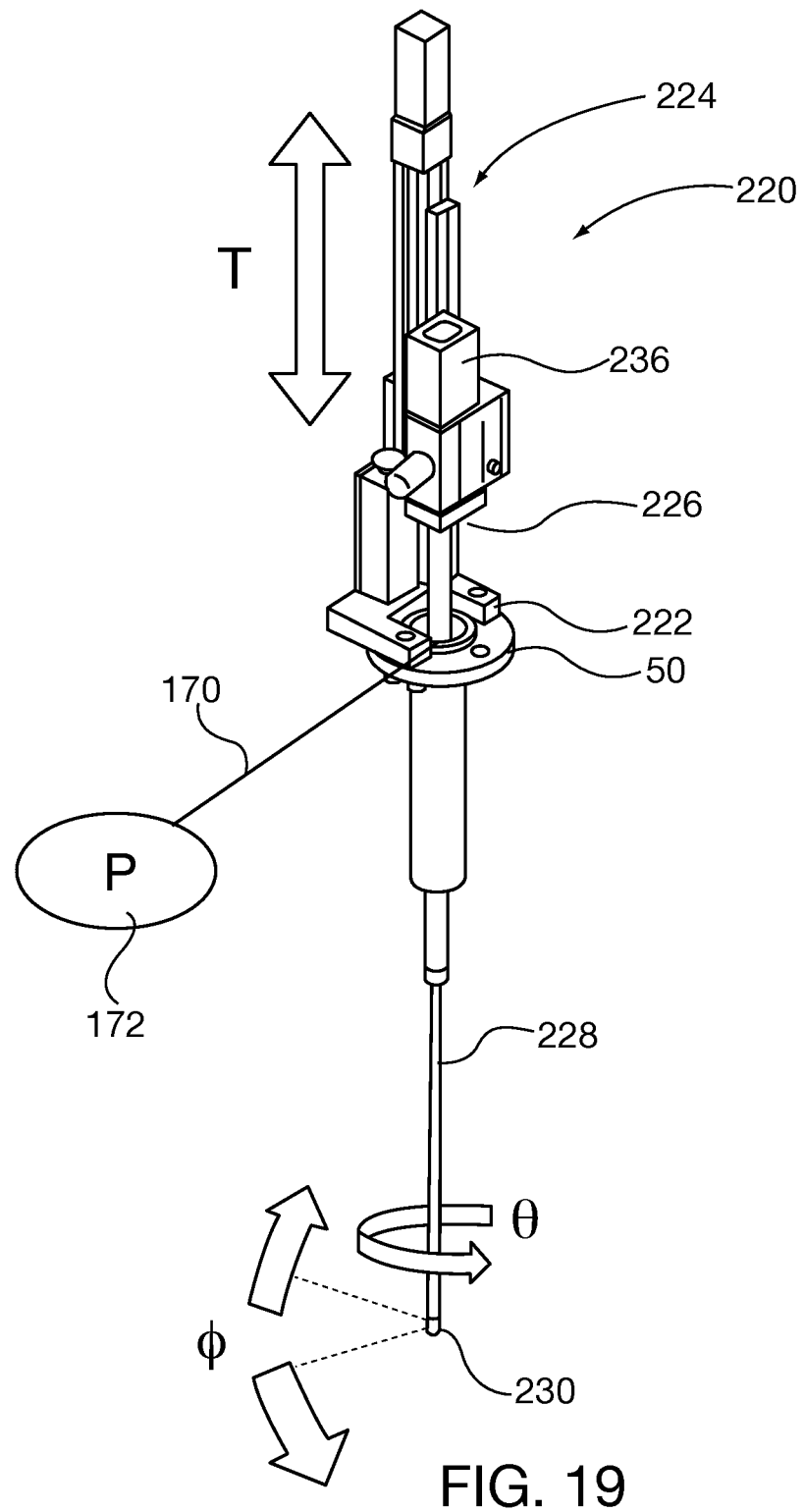
FIG. 19 is an elevational perspective view of optical camera inspection system embodiment of FIG. 18, showing available degrees of motion T, θ and Φ.
Figure 20:
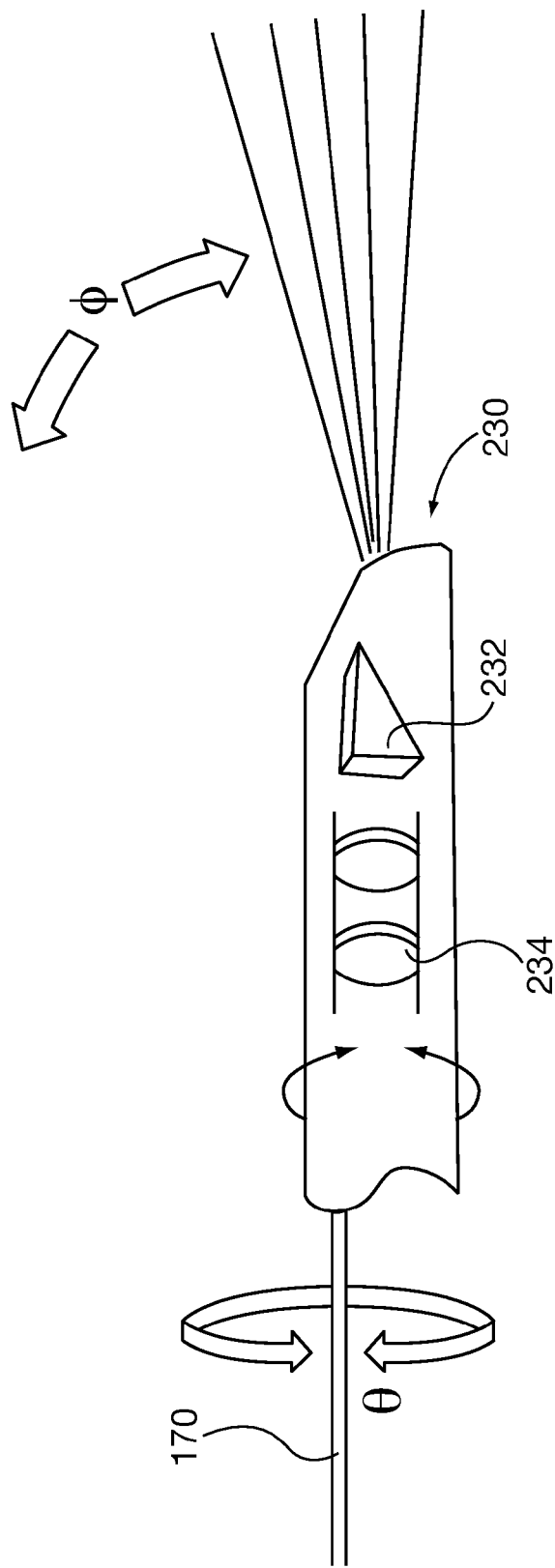
FIG. 20 is an elevational view of the swing prism articulation mechanism for the Φ degree of motion for the inspection system of FIG. 18.

A blade/vane inspection scope 220 embodiment is shown in FIGS. 18-20. This embodiment is particularly suitable for inspection within the confines of a gas turbine 30 turbine section 38, between rows of rotating blades and stationary vanes. FIG. 18 shows a pair of inspection scopes 220 respectively mounted to each of the Row 1 inspection port 50 and Row 2 inspection port 52. However, at the discretion of an inspection team, a single inspection scope 220 may be mounted to a selected inspection port or more than two inspection scopes 220 may be mounted to the turbine 30 simultaneously during an inspection procedure. Similarly, an inspection team at its discretion may also operate one or more of the inspection scope 60 embodiments simultaneously with or without the inspection scope 220 embodiment in any inspection procedure.

As shown in FIGS. 19 and 20 the inspection scope 220 embodiment is mounted to a gas turbine inspection port (here a Row 1 inspection port 50) by mounting flange 222. Linear drive 224 with an associated servomotor and encoder translates the inspection scope in the telescoping extension position, motion degree T. Rotational drive 226 with an associated servomotor and encoder rotates the inspection scope in the camera rotate/pan motion degree θ. Bore scope 228 is mechanically coupled to the linear drive 224 and rotational drive 226, and has a camera head 230 that captures within its field of view (FOV). The camera head 230 includes a pivoting prism 232 whose motion in the articulation Φ motion degree is imparted by an associated servomotor and encoder. The bore scope 228 is of known construction and includes fiber optic lenses 234 and auxiliary external lighting (not shown) that illuminate and transmit images within the camera head field of view to camera 236. The camera 236 may be an auto focusing USB camera that is coupled to a motion control system, such as shown in FIG. 16. General motion control and positioning of the inspection scope 220 along its motion degrees Φ, θ, and T and camera image capture are performed as previously described with respect to the inspection scope embodiment 50.

The inspection scope 220 includes an external cooling system for inspection within a turbine 30 cool-down phase when the turbine section 30 still has an elevated temperature of up to approximately 150° C. As was described with respect to the inspection scope embodiment 50, the cooling system includes an air line 170 running in parallel to or within the bore scope 228 that expels cooling air obtained from a cooling air source through one or more functional cooling air exhaust ports, such as around the camera head 230.

The three-motion degrees $\Phi$, $\theta$ and T in the blade/vane inspection scope 220 embodiment are sufficient to obtain complete images of the leading or trailing sides of all rotating turbine blades within a given row while the turbine rotor is spinning in turning gear mode. For example in FIG. 18 the leading side of each of the Row 1 turbine blades 44 can be inspected by the inspection scope 220 that is positioned in inspection port 50. As each individual blade rotates within the camera head 230 field of view, its image is captured by the associated control system. A partial or full series of blade images can be obtained during a single rotor 40 rotation while the turbine 30 is in turning gear mode. A single camera head 230 field of view may not capture the full radial length an area of interest on a turbine blade. By repositioning, the camera head tilt angle $\Phi$ or inserting/retracting the bore scope 228 along the T freedom degree the camera field of view can be repositioned radially along the blade or vane length. Images captured at different blade/vane radial positions can be combined to create an aggregate image of the entire blade. Similarly, an image of the trailing edge of each blade 44 in Row 1 can be captured by positioning an inspection scope 220 in turbine inspection port 52, as was done for the leading edges.

Exemplary Turbine Inspection Procedures, Including Surface Profile Inspection

The camera inspection systems 300, 300 or 400 optionally provide the capability of automatic positioning and image capture of an inspection camera or laser profilometer 410 field of view relative to an area of interest with a turbine, such as a gas turbine transition, blade or vane surface or blade tip gap, without human intervention. After inspection scope positioning sequence information is provided to the system, subsequent inspections are repeatable by different inspection teams, regardless of their individual inspection scope positioning skill or inspection speed. Automated inspections can be completed quicker, with less likelihood of human-created errors, as compared to known inspection procedures. Further explanation of the inspection methods of the present invention will be with reference to inspection of an exemplary industrial gas turbine.

Inspection scope positioning sequence information may be obtained by installing an inspection scope embodiment of the present invention on a selected inspection port and orienting all controlled motions to an initialized or "start" position. A human inspector guides the inspection scope through the control system HMI, e.g., by use of a joystick or touch screen pad, through a navigated path within the turbine that is recorded within one or both the control system controllers/host computer. The navigation path is chosen to orient the inspection scope's camera head and its field of view within area of interest without causing undesirable impact of the scope with turbine internal components.

The control system retains the navigation path information from the initial human-controlled inspection and can subsequently repeat the inspection scope positioning sequence for future inspection cycles on the same turbine or other turbines having the same internal structure. For example, a navigation path sequence can be performed on a single test turbine and the sequence can be communicated to other remote sites for use by inspection teams inspecting the same structure gas turbine located at that site. In the field, an inspection team may be concerned that a different gas turbine may have variations in internal structure from the original gas turbine. The field team may review the stored navigation path individual step by step, with local override to accommodate any needed path variations for the locally serviced turbine, or may choose to program a new navigation path dedicated to the field location turbine.

Navigation paths alternatively can be determined in virtual space by a human inspector simulating a navigation path in a simulated turbine and recording the path for subsequent use in actual turbine inspections. As another alternative, a scope inspection simulation program can prepare a suggested inspection navigation path for review and approval by a human inspector.

Figure 33:
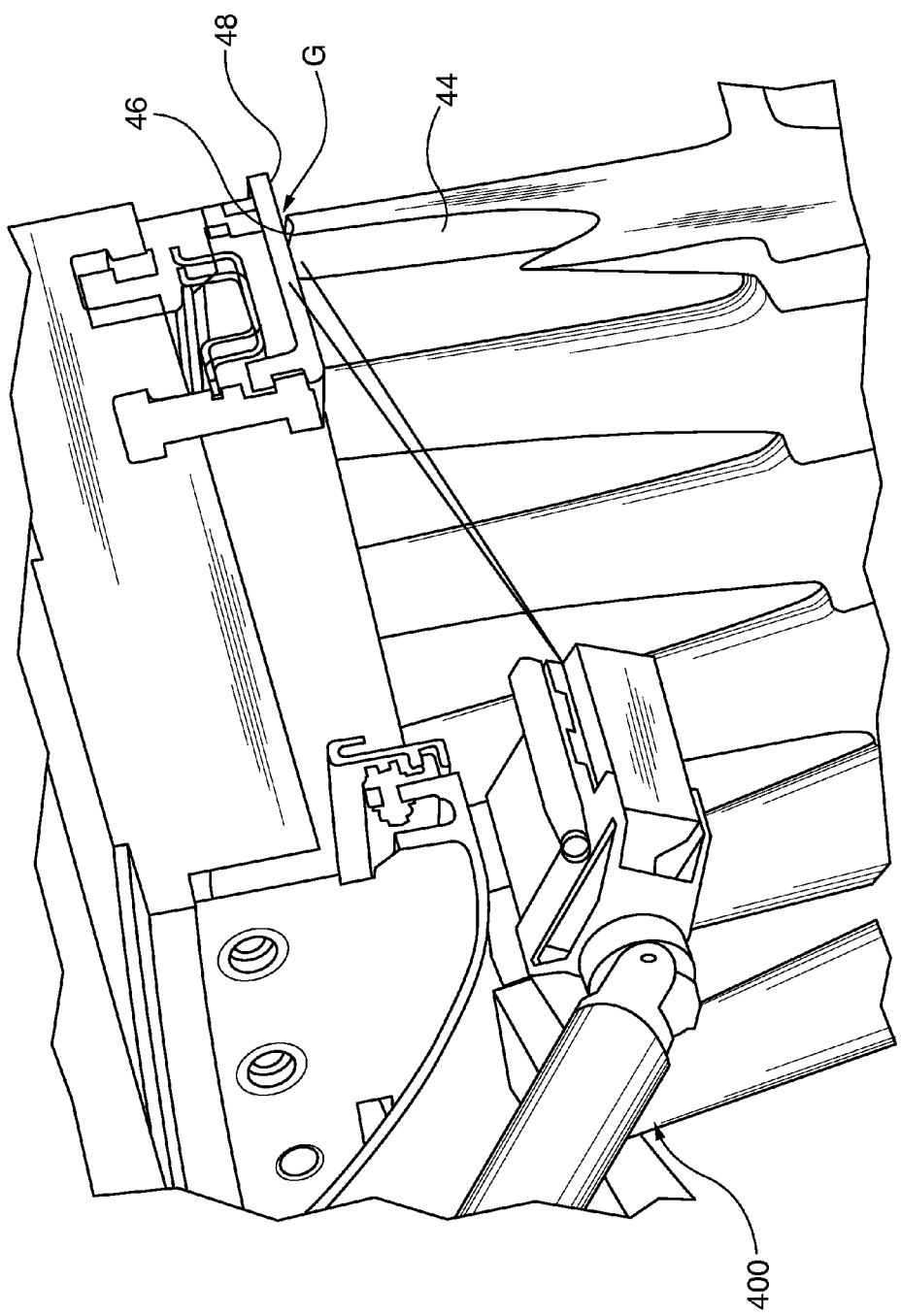
FIG. 33 is a perspective view of the inspection system of FIGS. 4 and 27 obtaining surface profile scan data of a combustion turbine section Row 1 turbine blade tip gap between the blade tip and its corresponding opposed circumferentially circumscribing turbine casing abradable surface, with the corresponding Row 1 opposing turbine vanes removed from the figure for easier reader viewing and comprehension of the blade tip gap measurement scan.

An automatically or manually controlled navigation path sequence can move the visual inspection system camera head 66, the 3D scanning system camera head 66' or the profilometer head 466 field of view from one position of interest to another position of interest. For example, as shown in FIG. 4, an inspection scope 60 can be affixed to a combustor nozzle port 36, whereupon the inspection system is advanced into the engine 30 interior, where it can capture and record relative surface profile height dimensional data of internal components within the combustor and its transition 37. As the inspection scope is advanced into the turbine section 38 the laser profilometer 410 and/or the camera 156 can acquire surface feature data about vanes 42 (see FIG. 32), or blades 44 (FIG. 33).

Figure 28:
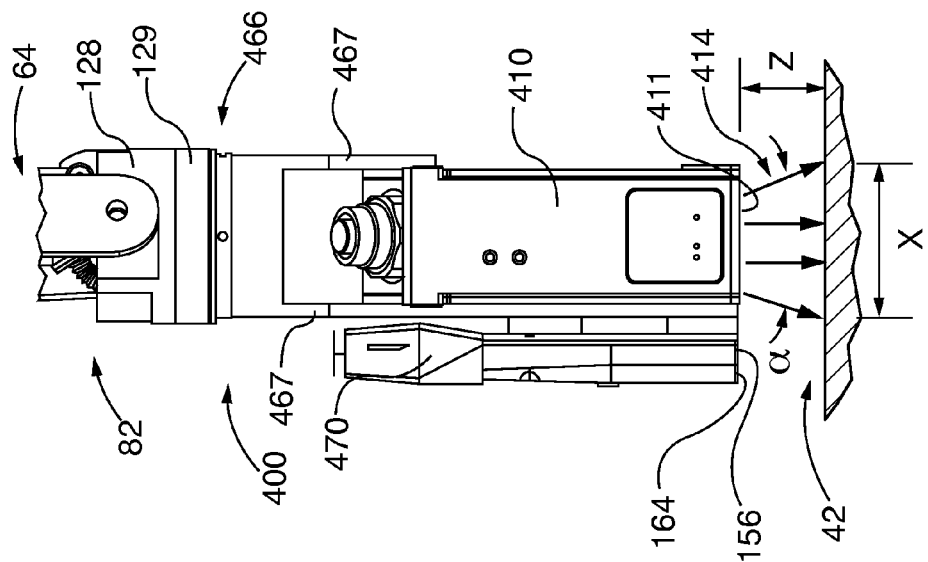
FIG. 28 is a top plan view of the laser profilometer head, including laser profilometer and optional external visual camera, of FIG. 27.
Figure 29:
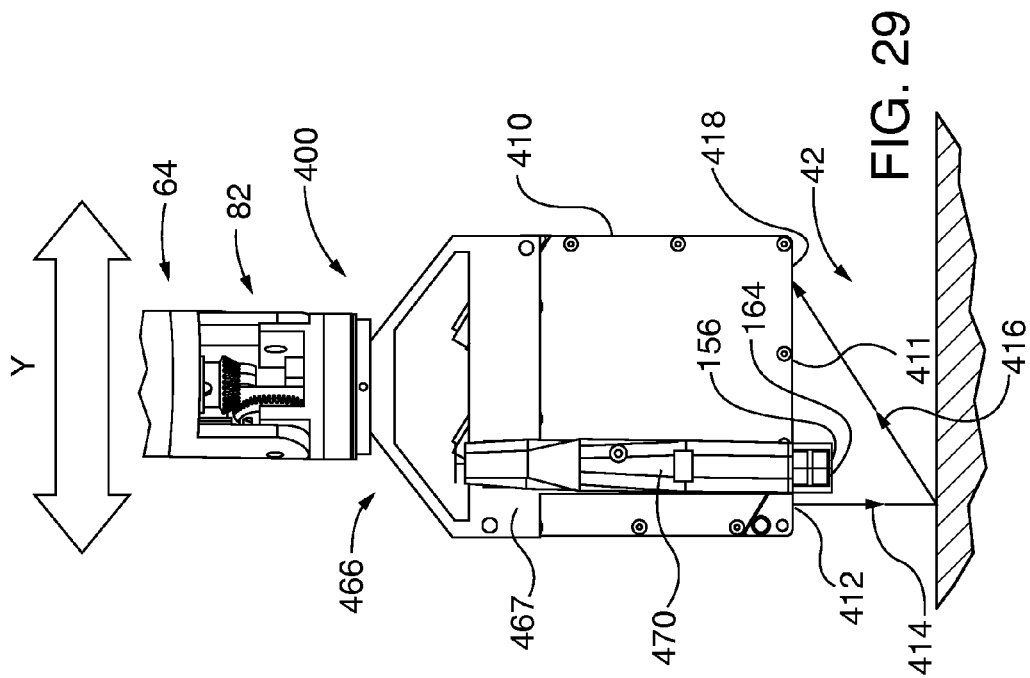
FIG. 29 is a side elevational view of the laser profilometer head, including laser profilometer and optional external visual camera, of FIG. 27.

Both visual image data and surface profile scan data may be combined in composite images. As shown in FIGS. 28 and 29 the laser profilometer 410 obtains a line of 2-D image data of width X at each scan position. Referring to FIGS. 34-38, 3-D surface profile scan data and relative dimensional height determinations are obtained by moving the profilometer 410 scan line field of view (FOV) relative to the vane surface 42 or any other component surface along direction Y by manipulating the inspection scope 60 motion control system.

Figure 36:
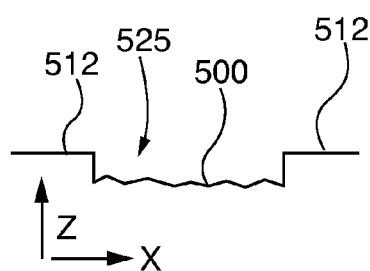
FIG. 36 is a graphical representation of relative height dimensional profile data obtained by the profilometer inspection system of the present invention in a single scan line of the surface defect of FIGS. 34 and 35.

Dimensional and qualitative information about the vane 42 surface condition are extracted from the compilation of the X by Y scan field. For example in FIG. 34 the vane 42 surface has spallation damage 500, where the thermal barrier coating (TBC) 510 has a crater-like depression 520 that does not extend fully to the underlying substrate surface 530. An exemplary profilometer 410-scan line 525 is shown in FIG. 36, which corresponds to the vane 42 cross section of FIG. 35. The scan line 525 contrasts the relative dimensional height differences between the undamaged surface portions 512 of the TBC from the cratered depth of the spallation zone 500. The imaging software operated in the main controller 200 personal computer can determine spallation zone dimensions with the scan data, which is useful for determining whether the subject vane 42 requires repair during an upcoming engine 30 scheduled maintenance cycle.

Figure 34:
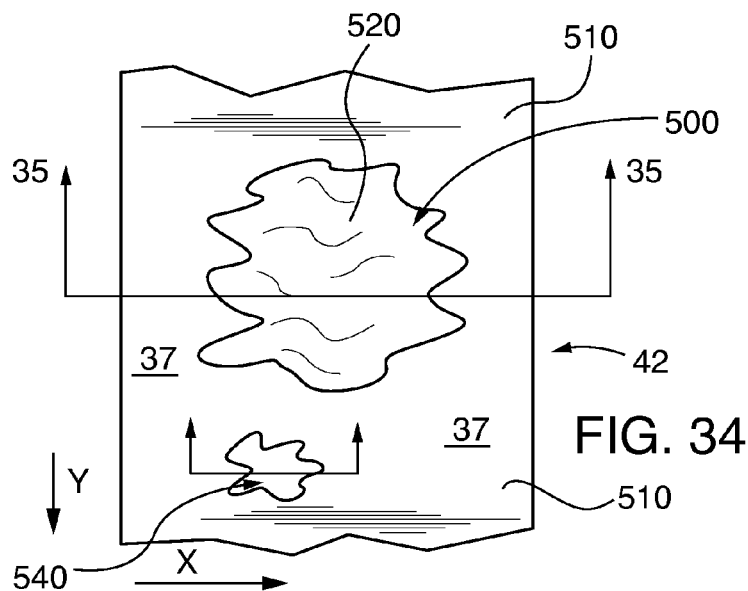
FIG. 34 is a schematic representation of a plan view of a power generation machine internal component surface defect, such as a turbine vane or blade thermal barrier coating spallation or delamination surface defect and a perforation defect through the thermal barrier coating and its underlying component substrate.
Figure 35:
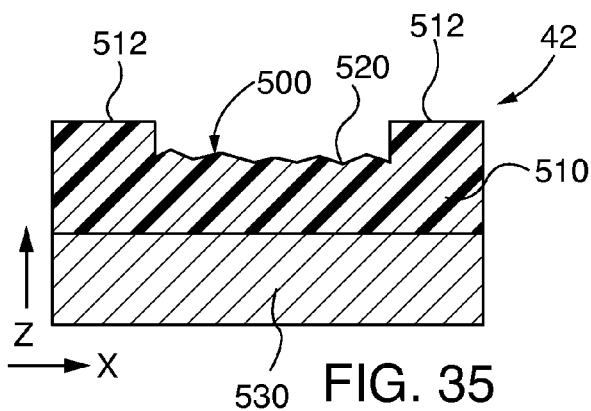
FIG. 35 is a cross-sectional view of the spallation or delamination surface defect of FIG. 34 taken along 35-35 thereof.
Figure 37:
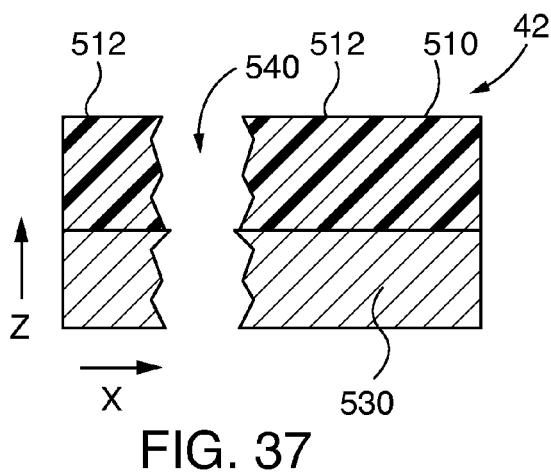
FIG. 37 is a cross-sectional view of the perforation defect of FIG. 34 taken along 37-37 thereof.
Figure 38:
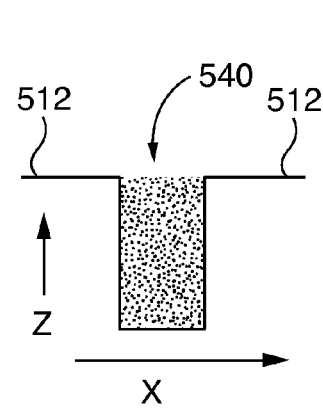
FIG. 38 is a graphical representation of relative height dimensional profile data obtained by the profilometer inspection system of the present invention in a single scan line of the perforation defect of FIGS. 34 and 37.

A profilometer 410 scan line or plurality of scan lines taken at different positions Y along the vane surface 42 can identify perforation holes, such as the hole 540 of FIGS. 34 and 37. Boundaries of the perforation 540 appear as gray noise, or no depth reading or a darkened corresponding zone in the scan image 545, as shown in FIG. 38. The relative distance between the boundary readings corresponds to perforation dimension along the scan line X. Advantageously, gaps between components, such as the blade tip gap G in FIG. 33 between the turbine blade tip 46 and its corresponding turbine casing circumferential abradable surface 48 also appear as a non-readable dead zone. Therefore blade tip gap G is determined by relative distance between the opposed blade tip 46 and abradable surface 48 boundary readings in a corresponding profilometer 410 scan line across the gap, the non-readable dead zone corresponding to the gap width.

When in a navigation path position the profilometer head 466 may be repositioned to obtain image information from different camera fields of view from the same reference position: for example by inserting the profilometer head 466 axially to a desired reference position and then rotating/panning the camera head 360 degrees about the entire inner circumference of transition 37 or any desired circumferential segment thereof. The various visual and/or 3D scanning images taken from the same reference point can be combined to obtain a composite or "stitched" view of the structural elements, or to take a virtual "tour" of any or all portions of the turbine interior.

Rather than move the camera head field of view from one position to another, it is also possible to move the turbine component areas of interest within the field of view of a stationary camera head. For example, as shown in FIG. 33, an inspection scope inserted between blade and vane rows can capture an image of each blade rotating within the camera field of view—in order to determine blade tip gap G of one or more blades in a given blade row relative to a desire circumferential position within the turbine engine casing—whether the turbine is in turning gear mode or whether an operator manually "bumps" each blade of a completely stopped turbine rotor sequentially in front of the camera head. The blade tip gap G determination procedure can be repeated at other circumferential positions about the engine casing, for example to determine engine casing warpage and/or individual blade variations in blade tip gap G at specific circumferential locations.

Although various embodiments, which incorporate the teachings of the present invention, have been shown and described in detail herein, those skilled in the art can readily devise many other varied embodiments that still incorporate these teachings. For example, "optical images" of turbine internal component can be obtained in the visible light spectrum or in the infrared spectrum. The inspection scope motion degrees do not have to be limited to those exemplary motions enabled by the servomotors 104 (Ω), 110 (T), 124 (θ), 124 (Φ), and 140 (E). Scope motion does not have to be imparted by servomotors, and can include known alternative pneumatic or other motion control systems.

What is claimed is:

1. A method for non-contact, internal inspection, including relative height sizing of component surface profiles, within an assembled power generation machine; the method comprising:
   providing an internal inspection system apparatus having:
     a base;
     an inspection scope having a proximal end for coupling to the base; an extendable elongated body defining a central axis, extended and driven by a linear drive that is capable of remote actuation by a control system; and a distal end that is insertable into an inspection port of and maneuvering within an internal cavity of an assembled power generation machine to an internal area of interest;
     a laser profilometer head, coupled to the inspection scope distal end, including a laser profilometer having a two-dimensional height and width scanning field of view that is capable of remote scanning field image capture by, and image transmission to a control system; and
     a control system coupled to the linear drive and the laser profilometer, for maneuvering the laser profilometer scanning field of view to an area of interest within the assembled power generation machine by actuation of the linear drive, for capturing a scanning field of view image thereof, and for converting said image into relative two-dimensional height/width relative sizing data;
   providing an assembled power generation machine having an inspection port that is in communication with an internal cavity and internal area of interest in the machine;
   attaching the base to the machine in a fixed position relative to the inspection port;
   inserting the inspection scope distal end, including the laser profilometer head, into the inspection port;
   coupling the inspection scope proximal end to the base;
   maneuvering the laser profilometer scanning field of view within the internal cavity to an internal area of interest by actuating the linear drive with the control system;
   capturing a scanning field of view image data of the area of interest by actuating the laser profilometer with the control system;
   transferring the captured image data to the control system; and
   converting the captured image data into two-dimensional height/width relative sizing data of the area of interest with the control system.

2. The method of claim 1, further comprising identifying component surface features, including perforations in surfaces, surface coating spallation, surface coating delamination, or gaps between opposed surfaces, including tip gap, with the two-dimensional sizing data.

3. The method of claim 1, further comprising converting the captured image data into a two-dimensional height/width relative sizing, surface profile map.

4. The method of claim 1, further comprising generating three-dimensional height/width/length relative sizing data of the area of interest, by:
   moving the scanning field of view relative to the surface of the area of interest by actuating the linear drive with the control system;
   capturing a plurality of scanning field of view images data at multiple spatial positions along a drive path of the linear drive by actuating the laser profilometer with the control system;
   transferring the plurality of captured images data to the control system; and
   converting the plurality of captured images data into a three-dimensional height/width/length relative sizing data of the area of interest with the control system.

5. The method of claim 4, further comprising identifying component surface features, including perforations in surfaces, surface coating spallation, surface coating delamination, or gaps between opposed surfaces, with the three-dimensional sizing data.

6. The method of claim 5, further comprising determining relative cross sectional area dimensions of component surface features with the three-dimensional sizing data.

7. The method of claim 4, further comprising converting the captured image data into a three-dimensional height/width/length relative sizing surface profile map with the control system.

8. The method of claim 1, further comprising:
   the provided inspection system further including:
     the base having a mounting flange for affixation to an inspection port;
     the inspection scope further having a rotational drive coupled to the control system and the laser profilometer head, and an articulation drive coupled to the control system and the laser profilometer head, for rotating and articulating the laser profilometer scanning field relative to the inspection scope centerline axis; and maneuvering the laser profilometer scanning field of view within the internal cavity to an internal area of interest by actuating the rotational or articulation drives with the control system.

9. A method for measuring blade tip gap in an assembled turbine engine power generation machine, having an inspection port in communication with open inter-row spacing volume between an opposing turbine vane and turbine blade row, comprising:

providing an assembled turbine engine, having an inspection port in communication with open inter-row spacing volume between an opposing turbine vane and turbine blade row;

providing an internal inspection system apparatus having:
a base;
an inspection scope having a proximal end for coupling to the base; an extendable elongated body defining a central axis, extended and driven by a linear drive that is capable of remote actuation by a control system; and a distal end that is insertable into an inspection port of, and maneuvering within an internal cavity of an assembled power generation machine to an internal area of interest;

a laser profilometer head, coupled to the inspection scope distal end, including a laser profilometer having a two-dimensional height and width scanning field of view that is capable of remote scanning field image capture by, and image transmission to a control system; and a control system coupled to the linear drive and the laser profilometer, for maneuvering the laser profilometer scanning field of view to an area of interest within the assembled power generation machine by actuation of the linear drive, for capturing a scanning field of view image thereof, and for converting said image into two-dimensional height/width relative sizing data;

inserting and coupling the inspection scope to the engine in a fixed position relative to the inter-row communicating inspection port;

maneuvering the laser profilometer scanning field of view within the inter-row spacing volume to scan turbine blade tip gap defined between a turbine blade tip surface and its corresponding opposed circumferential abradable surface of the turbine engine casing, by actuating the linear drive with the control system;

capturing the tip gap scanning field of view image data by actuating the laser profilometer with the control system;

transferring the corresponding tip gap captured image data to the control system;

converting the captured image data into a two-dimensional height/width relative sizing data of the corresponding blade tip and abradable opposed surfaces defining the tip gap; and determining blade tip gap with the relative sizing data.

10. The method of claim 9, further comprising generating a three-dimensional height/width/length relative sizing surface profile map of the blade tip gap, by:

moving the scanning field of view relative to the corresponding blade tip and abradable opposed surfaces defining the tip gap by actuating the linear drive with the control system;

capturing a plurality of scanning field of view images data at multiple spatial positions along a drive path of the linear drive by actuating the laser profilometer with the control system;

transferring the plurality of captured images data to the control system; and converting the plurality of captured images data into a three-dimensional height/width/length relative sizing surface profile map of the blade tip gap with the control system.

11. The method of claim 9, further comprising, sequentially rotating respective blade tips into the tip gap-scanning field and for each respective corresponding blade:

capturing corresponding tip gap scanning image data;
converting the captured image data into a two-dimensional height/width relative sizing data of the corresponding blade tip and abradable opposed surface defining the tip gap; and determining blade tip gap with the relative sizing data for each respective blade.

12. The method of claim 9, further comprising measuring blade tip gap at plural circumferential positions around the abradable surface by:

maneuvering the laser profilometer scanning field of view within the inter-row spacing volume to scan turbine blade tip gap at plural circumferential locations along the opposed circumferential abradable surface of the turbine engine casing, by actuating the linear drive with the control system and/or inserting and coupling the inspection scope sequentially to a plurality of inter-row communicating inspection ports that are oriented circumferentially along turbine engine casing;

for each respective scanning field circumferential location:

capturing the tip gap scanning field of view image data by actuating the laser profilometer with the control system;

transferring the corresponding tip gap captured image data to the control system;

converting the captured image data into a two-dimensional height/width relative sizing data of the corresponding blade tip and abradable opposed surface defining the tip gap; and determining blade tip gap with the relative sizing data.

13. The method of claim 9, further comprising:
the provided inspection system further including:
the base having a mounting flange for affixation to an inspection port;

the inspection scope further having a rotational drive coupled to the control system and the laser profilometer head, and an articulation drive coupled to the control system and the laser profilometer head, for rotating and articulating the laser profilometer scanning field relative to the inspection scope centerline axis; and maneuvering the laser profilometer scanning field of view within the within the inter-row spacing volume by actuating the rotational or articulation drives with the control system.

14. A system for non-contact, internal inspection, including relative height sizing of component surface profiles, within an assembled power generation machine; the system comprising:

a base for affixation to a power generation machine inspection port;

an inspection scope having a proximal end coupled to the base; an extendable elongated body defining a central axis, extended and driven by a linear drive that is capable of remote actuation by a control system; and a distal end that is insertable into an inspection port of and maneuvering within an internal cavity of an assembled power generation machine to an internal area of interest;

a laser profilometer head, coupled to the inspection scope distal end, including a laser profilometer having a two-dimensional height and width scanning field of view that is capable of remote scanning field image capture by, and image transmission to a control system; and a control system coupled to the linear drive and the laser profilometer, for maneuvering the laser profilometer scanning field of view to an area of interest within the assembled power generation machine by actuation of the linear drive, for capturing a scanning field of view image thereof, and for converting said image into two-dimensional height/width relative sizing data.

15. The system of claim 14, further comprising the control system capturing plural scanning field of view images, while moving the scanning field of view relative to a surface of the area of interest by actuating the linear drive, and converting the plural images into three-dimensional height/width/length relative sizing data.

16. The system of claim 14, further comprising:
a gas turbine engine, power generation machine, having an inspection port in communication with an open inter-row spacing volume between an opposing turbine vane and turbine blade row;
areas of interest including outer surfaces of turbine vane, turbine blades, and tip gap between turbine blade tips and their corresponding opposed circumferential abradable surface of the turbine engine casing; and
the control system identifying component surface features, including perforations in surfaces, surface coating spallation, surface coating delamination, or gaps between opposed surfaces, including tip gap, with the two-dimensional height/width relative sizing data.

17. The system of claim 14, further comprising:
the base including a mounting flange for affixation to an inspection port;
the inspection scope further having a rotational drive coupled to the control system and the laser profilometer head, for rotating the laser profilometer head scanning field about the central axis; and an articulation drive coupled to the control system and the laser profilometer head, for articulating the laser profilometer head scanning field relative to the central axis; and
the control system coupled to the rotational and articulation drives for rotating and articulating the laser profilometer scanning field relative to the inspection scope centerline axis.

18. The system of claim 17, further comprising:
the laser profilometer having a scanning face for projection of the scanning field;
the laser profilometer head including a profilometer bracket coupling the profilometer to the scope distal end.

19. The system of claim 18, further comprising a camera coupled to the profilometer bracket.

20. The system of claim 14, further comprising:
the laser profilometer having a scanning face for projection of the scanning field;
the laser profilometer head including a profilometer bracket coupling the profilometer to the scope distal end;
a camera coupled to the profilometer bracket; and
an illumination source coupled to the profilometer bracket.

* * * * *